(12) United States Patent
Hoffman et al.

(10) Patent No.: US 7,846,107 B2
(45) Date of Patent: Dec. 7, 2010

(54) ENDOSCOPIC APPARATUS WITH INTEGRATED MULTIPLE BIOPSY DEVICE

(75) Inventors: David W. Hoffman, Westborough, MA (US); Christopher Rowland, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/129,561

(22) Filed: May 13, 2005

(65) Prior Publication Data

US 2006/0258955 A1 Nov. 16, 2006

(51) Int. Cl.
*A61B 5/00* (2006.01)
(52) U.S. Cl. .................................................... 600/561
(58) Field of Classification Search ................. 600/561, 600/141, 146, 179, 459, 564, 567; 606/141, 606/167
See application file for complete search history.

(56) References Cited

U.S. PATENT DOCUMENTS

| | | | |
|---|---|---|---|
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 4,108,211 A | 8/1978 | Tanaka | |
| 4,286,585 A | 9/1981 | Ogawa | |
| 4,294,162 A | 10/1981 | Fowler et al. | |
| 4,315,309 A | 2/1982 | Coli | |
| 4,351,323 A | 9/1982 | Ouchi et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. | |
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,559,928 A | 12/1985 | Takayama | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |

(Continued)

FOREIGN PATENT DOCUMENTS

EP 0 689 851 A1 1/1996

(Continued)

*Primary Examiner*—Max Hindenburg
*Assistant Examiner*—Fangemonique Smith
(74) *Attorney, Agent, or Firm*—Finnegan Henderson Farabow Garrett & Dunner, L.L.P.

(57) ABSTRACT

An imaging endoscope comprising a shaft having a proximal end adapted to be secured to a handle, and a distal end having a biopsy forceps disposed therein. The biopsy forceps includes one or more end-effector elements that are actuated with a control cable that may be connected to the handle. The endoscope shaft includes a biopsy sample lumen that is configured to receive a biopsy sample obtained from the forceps assembly. A sample collection apparatus is attached to the handle to capture multiple biopsy samples. In some embodiments, the endoscope is a single-use endoscope.

27 Claims, 13 Drawing Sheets

U.S. PATENT DOCUMENTS

| | | |
|---|---|---|
| 4,616,630 A | 10/1986 | Arakawa |
| 4,617,915 A | 10/1986 | Arakawa |
| 4,621,618 A | 11/1986 | Omagari et al. |
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okobe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoki et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,081,524 A | 1/1992 | Tsuruoka et al. |
| 5,087,989 A | 2/1992 | Igarashi |
| 5,110,645 A | 5/1992 | Matsumoto et al. |
| 5,111,281 A | 5/1992 | Sekiguchi |
| 5,111,306 A | 5/1992 | Kanno et al. |
| 5,111,804 A | 5/1992 | Funakoshi |
| 5,113,254 A | 5/1992 | Kanno et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,159,446 A | 10/1992 | Hibino et al. |
| 5,170,775 A | 12/1992 | Tagami |
| 5,172,225 A | 12/1992 | Takahashi et al. |
| 5,174,293 A | 12/1992 | Hagiwara |
| 5,176,629 A | 1/1993 | Kullas et al. |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,291,010 A | 3/1994 | Tsuji |
| 5,299,559 A | 4/1994 | Bruce et al. |
| 5,311,858 A | 5/1994 | Adair |
| 5,325,845 A | 7/1994 | Adair et al. |

| | | | | | |
|---|---|---|---|---|---|
| 5,331,551 A | 7/1994 | Tsuruoka et al. | 5,805,140 A | 9/1998 | Rosenberg et al. |
| 5,342,299 A | 8/1994 | Snoke et al. | 5,810,715 A | 9/1998 | Moriyama |
| 5,347,989 A | 9/1994 | Monroe et al. | 5,812,983 A | 9/1998 | Kumagai |
| 5,374,953 A | 12/1994 | Sasaki et al. | 5,819,736 A | 10/1998 | Avny et al. |
| 5,379,757 A | 1/1995 | Hiyama et al. | 5,820,591 A | 10/1998 | Thompson et al. |
| 5,381,782 A | 1/1995 | DeLaRama et al. | 5,821,466 A | 10/1998 | Clark et al. |
| 5,390,662 A | 2/1995 | Okada | 5,821,920 A | 10/1998 | Rosenberg et al. |
| 5,400,769 A | 3/1995 | Tanii et al. | 5,823,948 A | 10/1998 | Ross, Jr. et al. |
| 5,402,768 A | 4/1995 | Adair | 5,827,186 A | 10/1998 | Chen et al. |
| 5,402,769 A | 4/1995 | Tsuji | 5,827,190 A | 10/1998 | Palcic et al. |
| 5,409,485 A | 4/1995 | Suda | 5,828,197 A | 10/1998 | Martin et al. |
| 5,412,478 A | 5/1995 | Ishihara et al. | 5,828,363 A | 10/1998 | Yaniger et al. |
| 5,418,649 A | 5/1995 | Igarashi | 5,830,124 A | 11/1998 | Suzuki et al. |
| 5,420,644 A | 5/1995 | Watanabe | 5,830,128 A | 11/1998 | Tanaka |
| 5,431,645 A | 7/1995 | Smith et al. | 5,836,869 A | 11/1998 | Kudo et al. |
| 5,434,615 A | 7/1995 | Matsumoto | 5,837,023 A | 11/1998 | Koike et al. |
| 5,436,640 A | 7/1995 | Reeves | 5,840,014 A | 11/1998 | Miyano et al. |
| 5,436,767 A | 7/1995 | Suzuki et al. | 5,841,126 A | 11/1998 | Fossum et al. |
| 5,440,341 A | 8/1995 | Suzuki et al. | 5,843,000 A | 12/1998 | Nishioka et al. |
| 5,464,007 A | 11/1995 | Krauter et al. | 5,846,183 A | 12/1998 | Chilcoat |
| 5,469,840 A | 11/1995 | Tanii et al. | 5,848,978 A * | 12/1998 | Cecchi ...................... 600/567 |
| 5,473,235 A | 12/1995 | Lance et al. | 5,855,560 A | 1/1999 | Idaomi et al. |
| 5,482,029 A | 1/1996 | Sekiguchi et al. | 5,857,963 A | 1/1999 | Pelchy et al. |
| 5,484,407 A | 1/1996 | Osypka | 5,865,724 A | 2/1999 | Palmer et al. |
| 5,485,316 A | 1/1996 | Mori et al. | 5,868,664 A | 2/1999 | Speier et al. |
| 5,496,260 A | 3/1996 | Krauter et al. | 5,868,666 A | 2/1999 | Okada et al. |
| 5,507,296 A | 4/1996 | Bales et al. | 5,871,453 A | 2/1999 | Banik et al. |
| 5,515,449 A | 5/1996 | Tsuruoka et al. | 5,873,816 A | 2/1999 | Kagawa et al. |
| 5,518,501 A | 5/1996 | Oneda et al. | 5,873,866 A | 2/1999 | Kondo et al. |
| 5,524,634 A | 6/1996 | Turkel et al. | 5,876,326 A | 3/1999 | Takamura et al. |
| 5,538,008 A | 7/1996 | Crowe | 5,876,331 A | 3/1999 | Wu et al. |
| 5,543,831 A | 8/1996 | Tsuji et al. | 5,876,373 A | 3/1999 | Giba et al. |
| 5,569,158 A | 10/1996 | Suzuki et al. | 5,876,427 A | 3/1999 | Chen et al. |
| 5,569,159 A | 10/1996 | Anderson et al. | 5,877,819 A | 3/1999 | Branson |
| 5,586,262 A | 12/1996 | Komatsu et al. | 5,879,284 A | 3/1999 | Tsujita |
| 5,589,854 A | 12/1996 | Tsai | 5,880,714 A | 3/1999 | Rosenberg et al. |
| 5,591,202 A | 1/1997 | Slater et al. | 5,882,293 A | 3/1999 | Ouchi |
| 5,608,451 A | 3/1997 | Konno et al. | 5,882,339 A | 3/1999 | Beiser et al. |
| 5,619,380 A | 4/1997 | Agasawa et al. | 5,889,670 A | 3/1999 | Schuler et al. |
| 5,622,528 A | 4/1997 | Hamano et al. | 5,889,672 A | 3/1999 | Schuler et al. |
| 5,631,695 A | 5/1997 | Nakamura et al. | 5,892,630 A | 4/1999 | Broome |
| 5,633,203 A | 5/1997 | Adair | 5,895,350 A | 4/1999 | Hori |
| 5,643,203 A | 7/1997 | Beiser et al. | 5,897,507 A | 4/1999 | Kortenbach et al. |
| 5,645,075 A | 7/1997 | Palmer et al. | 5,897,525 A | 4/1999 | Dey et al. |
| 5,647,840 A | 7/1997 | D'Amelio et al. | 5,907,487 A | 5/1999 | Rosenberg et al. |
| 5,658,238 A | 8/1997 | Suzuki et al. | 5,916,175 A | 6/1999 | Bauer |
| 5,666,965 A | 9/1997 | Bales et al. | 5,923,018 A | 7/1999 | Kameda et al. |
| 5,667,477 A | 9/1997 | Segawa | 5,928,136 A | 7/1999 | Barry |
| 5,674,182 A | 10/1997 | Suzuki et al. | 5,929,607 A | 7/1999 | Rosenberg et al. |
| 5,674,197 A | 10/1997 | van Muiden et al. | 5,929,846 A | 7/1999 | Rosenberg et al. |
| 5,685,823 A | 11/1997 | Ito et al. | 5,929,900 A | 7/1999 | Yamanaka |
| 5,685,825 A | 11/1997 | Takase et al. | 5,929,901 A | 7/1999 | Adair et al. |
| 5,691,853 A | 11/1997 | Miyano | 5,931,833 A | 8/1999 | Silverstein |
| 5,695,450 A | 12/1997 | Yabe et al. | 5,933,809 A | 8/1999 | Hunt et al. |
| 5,698,866 A | 12/1997 | Doiron et al. | 5,935,085 A | 8/1999 | Welsh et al. |
| 5,702,349 A | 12/1997 | Morizumi | 5,936,778 A | 8/1999 | Miyano et al. |
| 5,703,724 A | 12/1997 | Miyano | 5,941,817 A | 8/1999 | Crawford |
| 5,704,371 A | 1/1998 | Shepard | 5,950,168 A | 9/1999 | Simborg et al. |
| 5,704,896 A | 1/1998 | Fukunishi et al. | 5,951,462 A | 9/1999 | Yamanaka |
| 5,707,392 A | 1/1998 | Kortenbach | 5,951,489 A | 9/1999 | Bauer |
| 5,708,482 A | 1/1998 | Takahashi et al. | 5,956,416 A | 9/1999 | Tsuruoka et al. |
| 5,721,566 A | 2/1998 | Rosenberg et al. | 5,956,689 A | 9/1999 | Everhart |
| 5,724,068 A | 3/1998 | Sanchez et al. | 5,956,690 A | 9/1999 | Haggerson et al. |
| 5,728,045 A | 3/1998 | Komi | 5,959,613 A | 9/1999 | Rosenberg et al. |
| 5,739,811 A | 4/1998 | Rosenberg et al. | 5,976,070 A | 11/1999 | Ono et al. |
| 5,740,801 A | 4/1998 | Branson | 5,976,074 A | 11/1999 | Moriyama |
| 5,746,696 A | 5/1998 | Kondo | 5,980,454 A | 11/1999 | Broome |
| 5,764,809 A | 6/1998 | Nomami et al. | 5,980,468 A | 11/1999 | Zimmon |
| 5,767,839 A | 6/1998 | Rosenberg | 5,986,693 A | 11/1999 | Adair et al. |
| 5,781,172 A | 7/1998 | Engel et al. | 5,991,729 A | 11/1999 | Barry et al. |
| 5,788,714 A | 8/1998 | Ouchi | 5,991,730 A | 11/1999 | Lubin et al. |
| 5,789,047 A | 8/1998 | Sasaki et al. | 5,999,168 A | 12/1999 | Rosenberg et al. |
| 5,793,539 A | 8/1998 | Konno et al. | 6,002,425 A | 12/1999 | Yamanaka et al. |

| | | | | | | |
|---|---|---|---|---|---|---|
| 6,007,531 | A | 12/1999 | Snoke et al. | 6,398,724 | B1 | 6/2002 | May et al. |
| 6,014,630 | A | 1/2000 | Jeacock et al. | 6,413,207 | B1 | 7/2002 | Minami |
| 6,015,088 | A | 1/2000 | Parker et al. | 6,421,078 | B1 | 7/2002 | Akai et al. |
| 6,017,322 | A | 1/2000 | Snoke et al. | 6,425,535 | B1 | 7/2002 | Akiba |
| 6,020,875 | A | 2/2000 | Moore et al. | 6,425,858 | B1 | 7/2002 | Minami |
| 6,020,876 | A | 2/2000 | Rosenberg et al. | 6,436,032 | B1 | 8/2002 | Eto et al. |
| 6,026,363 | A | 2/2000 | Shepard | 6,441,845 | B1 | 8/2002 | Matsumoto |
| 6,030,360 | A | 2/2000 | Biggs | 6,447,444 | B1 | 9/2002 | Avni et al. |
| 6,032,120 | A | 2/2000 | Rock et al. | 6,449,006 | B1 | 9/2002 | Shipp |
| 6,039,728 | A | 3/2000 | Berlien et al. | 6,453,190 | B1 | 9/2002 | Acker et al. |
| 6,043,839 | A | 3/2000 | Adair et al. | 6,454,162 | B1 | 9/2002 | Teller |
| 6,050,718 | A | 4/2000 | Schena et al. | 6,458,076 | B1 * | 10/2002 | Pruitt .................. 600/146 |
| 6,057,828 | A | 5/2000 | Rosenberg et al. | 6,459,447 | B1 | 10/2002 | Okada et al. |
| 6,059,719 | A | 5/2000 | Yamamoto et al. | 6,468,204 | B2 | 10/2002 | Sendai et al. |
| 6,061,004 | A | 5/2000 | Rosenberg | 6,475,141 | B2 | 11/2002 | Abe |
| 6,067,077 | A | 5/2000 | Martin et al. | 6,478,730 | B1 | 11/2002 | Bala et al. |
| 6,071,248 | A | 6/2000 | Zimmon | 6,489,987 | B1 | 12/2002 | Higuchi et al. |
| 6,075,555 | A | 6/2000 | Street | 6,496,827 | B2 | 12/2002 | Kozam et al. |
| 6,078,308 | A | 6/2000 | Rosenberg et al. | 6,498,948 | B1 | 12/2002 | Ozawa et al. |
| 6,078,353 | A | 6/2000 | Yamanaka et al. | 6,503,193 | B1 | 1/2003 | Iwasaki et al. |
| 6,078,876 | A | 6/2000 | Rosenberg et al. | 6,520,908 | B1 | 2/2003 | Ikeda et al. |
| 6,080,104 | A | 6/2000 | Ozawa et al. | 6,524,234 | B2 | 2/2003 | Ouchi |
| 6,081,809 | A | 6/2000 | Kumagai | 6,530,882 | B1 | 3/2003 | Farkas et al. |
| 6,083,152 | A | 7/2000 | Strong | 6,533,722 | B2 | 3/2003 | Nakashima |
| 6,083,170 | A | 7/2000 | Ben-Haim | 6,540,669 | B2 | 4/2003 | Abe et al. |
| 6,095,971 | A | 8/2000 | Takahashi | 6,544,194 | B1 | 4/2003 | Kortenbach et al. |
| 6,099,465 | A | 8/2000 | Inoue | 6,545,703 | B1 | 4/2003 | Takahashi et al. |
| 6,100,874 | A | 8/2000 | Schena et al. | 6,551,239 | B2 | 4/2003 | Renner et al. |
| 6,104,382 | A | 8/2000 | Martin et al. | 6,558,317 | B2 | 5/2003 | Takahashi et al. |
| 6,120,435 | A | 9/2000 | Eino | 6,561,971 | B1 | 5/2003 | Akiba |
| 6,125,337 | A | 9/2000 | Rosenberg et al. | 6,564,120 | B1 * | 5/2003 | Richard et al. .............. 700/214 |
| 6,128,006 | A | 10/2000 | Rosenberg et al. | 6,565,507 | B2 | 5/2003 | Kamata et al. |
| 6,132,369 | A | 10/2000 | Takahashi | 6,569,105 | B1 | 5/2003 | Kortenbach et al. |
| 6,134,056 | A | 10/2000 | Nakamuka | 6,574,629 | B1 | 6/2003 | Cooke, Jr. et al. |
| 6,134,506 | A | 10/2000 | Rosenberg et al. | 6,589,162 | B2 | 7/2003 | Nakashima et al. |
| 6,135,946 | A | 10/2000 | Konen et al. | 6,595,913 | B2 | 7/2003 | Takahashi |
| 6,139,508 | A | 10/2000 | Simpson et al. | 6,597,390 | B2 | 7/2003 | Higuchi |
| 6,141,037 | A | 10/2000 | Upton et al. | 6,599,239 | B2 | 7/2003 | Hayakawa et al. |
| 6,142,956 | A | 11/2000 | Kortenbach et al. | 6,602,186 | B1 | 8/2003 | Sugimoto et al. |
| 6,146,355 | A | 11/2000 | Biggs | 6,605,035 | B2 | 8/2003 | Ando et al. |
| 6,149,607 | A * | 11/2000 | Simpson et al. ............. 600/567 | 6,609,135 | B1 | 8/2003 | Omori et al. |
| 6,152,877 | A | 11/2000 | Masters | 6,611,846 | B1 | 8/2003 | Stoodley |
| 6,154,198 | A | 11/2000 | Rosenberg | 6,614,969 | B2 | 9/2003 | Eichelberger et al. |
| 6,154,248 | A | 11/2000 | Ozawa et al. | 6,616,601 | B2 | 9/2003 | Hayakawa |
| 6,155,988 | A | 12/2000 | Peters | 6,623,424 | B2 | 9/2003 | Hayakawa et al. |
| 6,174,292 | B1 | 1/2001 | Kortenbach | 6,632,182 | B1 * | 10/2003 | Treat .................. 600/564 |
| 6,181,481 | B1 | 1/2001 | Yamamoto et al. | 6,638,214 | B2 | 10/2003 | Akiba |
| 6,184,922 | B1 | 2/2001 | Saito et al. | 6,638,215 | B2 | 10/2003 | Kobayashi |
| 6,193,714 | B1 | 2/2001 | McGaffigan et al. | 6,641,528 | B2 | 11/2003 | Torii |
| 6,195,592 | B1 | 2/2001 | Schuler et al. | 6,651,669 | B1 | 11/2003 | Burnside |
| 6,203,493 | B1 | 3/2001 | Ben-Haim | 6,656,110 | B1 | 12/2003 | Irion et al. |
| 6,206,824 | B1 | 3/2001 | Ohara et al. | 6,656,112 | B2 | 12/2003 | Miyanaga |
| 6,211,904 | B1 | 4/2001 | Adair | 6,659,940 | B2 | 12/2003 | Adler |
| 6,216,104 | B1 | 4/2001 | Moshfeghi et al. | 6,663,561 | B2 | 12/2003 | Sugimoto et al. |
| 6,219,091 | B1 | 4/2001 | Yamanaka et al. | 6,669,629 | B2 | 12/2003 | Matsui |
| 6,221,070 | B1 | 4/2001 | Tu et al. | 6,669,643 | B1 * | 12/2003 | Dubinsky .................. 600/459 |
| 6,241,668 | B1 | 6/2001 | Herzog | 6,673,012 | B2 | 1/2004 | Fujii et al. |
| 6,260,994 | B1 | 7/2001 | Matsumoto et al. | 6,677,984 | B1 | 1/2004 | Kobayashi et al. |
| 6,264,617 | B1 | 7/2001 | Bales et al. | 6,678,397 | B1 | 1/2004 | Omori et al. |
| 6,272,470 | B1 | 8/2001 | Teshima | 6,682,479 | B1 | 1/2004 | Takahashi et al. |
| 6,275,255 | B1 | 8/2001 | Adair et al. | 6,685,631 | B2 | 2/2004 | Minami |
| 6,283,960 | B1 | 9/2001 | Ashley | 6,686,949 | B2 | 2/2004 | Kobayashi et al. |
| 6,295,082 | B1 | 9/2001 | Dowdy et al. | 6,690,409 | B1 | 2/2004 | Takahashi |
| 6,299,625 | B1 | 10/2001 | Bacher | 6,690,963 | B2 | 2/2004 | Ben-Haim et al. |
| 6,309,347 | B1 | 10/2001 | Takahashi et al. | 6,692,431 | B2 | 2/2004 | Kazakevich |
| 6,310,642 | B1 | 10/2001 | Adair et al. | 6,697,101 | B1 | 2/2004 | Takahashi et al. |
| 6,319,196 | B1 | 11/2001 | Minami | 6,699,181 | B2 | 3/2004 | Wako |
| 6,319,197 | B1 | 11/2001 | Tsuji et al. | 6,702,737 | B2 | 3/2004 | Hinto et al. |
| 6,322,522 | B1 | 11/2001 | Zimmon | 6,711,426 | B2 | 3/2004 | Benaron et al. |
| 6,334,844 | B1 | 1/2002 | Akiba | 6,715,068 | B1 | 3/2004 | Abe |
| 6,346,075 | B1 | 2/2002 | Arai et al. | 6,716,162 | B2 | 4/2004 | Hakamata |
| 6,366,799 | B1 | 4/2002 | Acker et al. | 6,728,599 | B2 | 4/2004 | Wang et al. |
| 6,381,029 | B1 | 4/2002 | Tipirneni | 6,730,018 | B2 | 5/2004 | Takase |

| | | | | | | |
|---|---|---|---|---|---|---|
| 6,736,773 B2 | 5/2004 | Wendlandt et al. | | 6,934,575 B2 | 8/2005 | Ferre et al. |
| 6,743,240 B2 | 6/2004 | Smith et al. | | 6,943,663 B2 | 9/2005 | Wang et al. |
| 6,749,559 B1 | 6/2004 | Krass et al. | | 6,943,946 B2 | 9/2005 | Fiete |
| 6,749,560 B1 | 6/2004 | Konstorum et al. | | 6,943,959 B2 | 9/2005 | Homma |
| 6,749,561 B2 | 6/2004 | Kazakevich | | 6,943,966 B2 | 9/2005 | Konno |
| 6,753,905 B1 | 6/2004 | Okada et al. | | 6,944,031 B2 | 9/2005 | Takami |
| 6,758,806 B2 | 7/2004 | Kamrava et al. | | 6,949,068 B2 | 9/2005 | Taniguchi et al. |
| 6,758,807 B2 | 7/2004 | Minami | | 6,950,691 B2 | 9/2005 | Uchikubo |
| 6,758,842 B2 | 7/2004 | Irion et al. | | 6,955,671 B2 | 10/2005 | Uchikubo |
| 6,778,208 B2 | 8/2004 | Takeshige et al. | | 2001/0039370 A1 | 11/2001 | Takahashi et al. |
| 6,780,151 B2 | 8/2004 | Grabover et al. | | 2001/0049491 A1 | 12/2001 | Shimada |
| 6,785,410 B2 | 8/2004 | Vining et al. | | 2002/0017515 A1 | 2/2002 | Obata et al. |
| 6,785,593 B2 | 8/2004 | Wang et al. | | 2002/0028984 A1 | 3/2002 | Hayakawa et al. |
| 6,796,938 B2 | 9/2004 | Sendai | | 2002/0055669 A1 | 5/2002 | Konno |
| 6,796,939 B1 | 9/2004 | Hirata et al. | | 2002/0080248 A1 | 6/2002 | Adair et al. |
| 6,798,533 B2 | 9/2004 | Tipirneni | | 2002/0087048 A1 | 7/2002 | Brock et al. |
| 6,800,056 B2 | 10/2004 | Tartaglia et al. | | 2002/0087166 A1 | 7/2002 | Brock et al. |
| 6,800,057 B2 | 10/2004 | Tsujita et al. | | 2002/0095175 A1 | 7/2002 | Brock et al. |
| 6,808,491 B2 | 10/2004 | Kortenbach et al. | | 2002/0128633 A1 | 9/2002 | Brock et al. |
| 6,824,539 B2 | 11/2004 | Novak | | 2002/0193664 A1 | 12/2002 | Ross et al. |
| 6,824,548 B2 | 11/2004 | Smith et al. | | 2003/0032863 A1 | 2/2003 | Kazakevich |
| 6,829,003 B2 | 12/2004 | Takami | | 2003/0069897 A1 | 4/2003 | Roy et al. |
| 6,830,545 B2 | 12/2004 | Bendall | | 2003/0073928 A1 | 4/2003 | Kortenbach et al. |
| 6,832,990 B2 | 12/2004 | Kortenbach et al. | | 2003/0149338 A1 | 8/2003 | Francois et al. |
| 6,840,932 B2 | 1/2005 | Lang | | 2003/0181905 A1 | 9/2003 | Long |
| 6,842,196 B1 | 1/2005 | Swift et al. | | 2004/0049097 A1 | 3/2004 | Miyake |
| 6,846,286 B2 | 1/2005 | Suzuki et al. | | 2004/0054258 A1 | 3/2004 | Maeda et al. |
| 6,847,933 B1 | 1/2005 | Hastings | | 2004/0059253 A1 | 3/2004 | Martone et al. |
| 6,849,043 B2 | 2/2005 | Kondo | | 2004/0073083 A1 | 4/2004 | Ikeda et al. |
| 6,850,794 B2 | 2/2005 | Shahidi | | 2004/0073084 A1 | 4/2004 | Maeda et al. |
| 6,855,109 B2 | 2/2005 | Obata et al. | | 2004/0073085 A1 | 4/2004 | Ikeda et al. |
| 6,858,004 B1 | 2/2005 | Ozawa et al. | | 2004/0147809 A1 | 7/2004 | Kazakevich |
| 6,858,014 B2 | 2/2005 | Damarati | | 2004/0167379 A1 | 8/2004 | Akiba |
| 6,860,849 B2 | 3/2005 | Matsushita et al. | | 2004/0183010 A1 | 9/2004 | Reilly et al. |
| 6,863,650 B1 | 3/2005 | Irion | | 2004/0249247 A1 | 12/2004 | Iddan |
| 6,863,661 B2 | 3/2005 | Carrillo et al. | | 2004/0257608 A1 | 12/2004 | Tipirneni |
| 6,868,195 B2 | 3/2005 | Fujita | | 2005/0197536 A1* | 9/2005 | Banik et al. ................. 600/179 |
| 6,871,086 B2 | 3/2005 | Nevo et al. | | 2005/0197861 A1 | 9/2005 | Omori et al. |
| 6,873,352 B2 | 3/2005 | Mochida et al. | | 2005/0203341 A1 | 9/2005 | Welker et al. |
| 6,876,380 B2 | 4/2005 | Abe et al. | | 2005/0228697 A1 | 10/2005 | Funahashi |
| 6,879,339 B2 | 4/2005 | Ozawa | | | | |
| 6,881,188 B2 | 4/2005 | Furuya et al. | | | | |

FOREIGN PATENT DOCUMENTS

| | | |
|---|---|---|
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 A | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 3219521 B2 | 8/2001 |
| JP | 2002-102152 A2 | 4/2002 |
| JP | 2002-177197 A2 | 6/2002 |
| JP | 2002-185873 A2 | 6/2002 |
| JP | 2002-253481 A2 | 9/2002 |
| JP | 3372273 B2 | 11/2002 |
| JP | 2003-075113 A2 | 3/2003 |
| JP | 3482238 B2 | 10/2003 |
| WO | WO 93/13704 A1 | 7/1993 |
| WO | WO 98/33436 A1 | 8/1998 |
| WO | WO 99/07288 A1 | 2/1999 |
| WO | WO 2004/016310 A2 | 2/2004 |
| WO | WO 2005/023082 A2 | 3/2005 |
| WO | WO 2006/038634 A1 | 4/2006 |

* cited by examiner

| | | |
|---|---|---|
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayahi et al. |
| 6,932,761 B2 | 8/2005 | Maeda et al. |
| 6,934,093 B2 | 8/2005 | Kislev et al. |

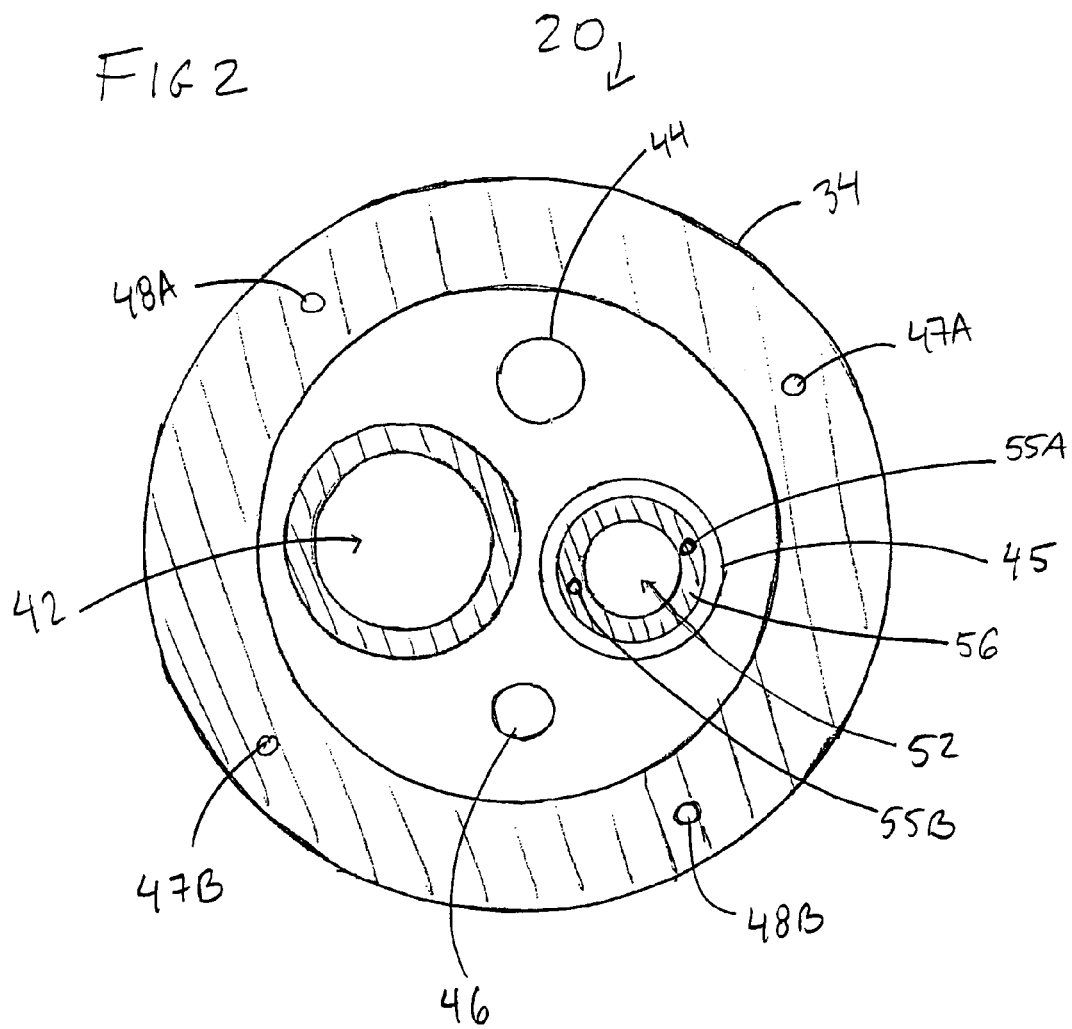

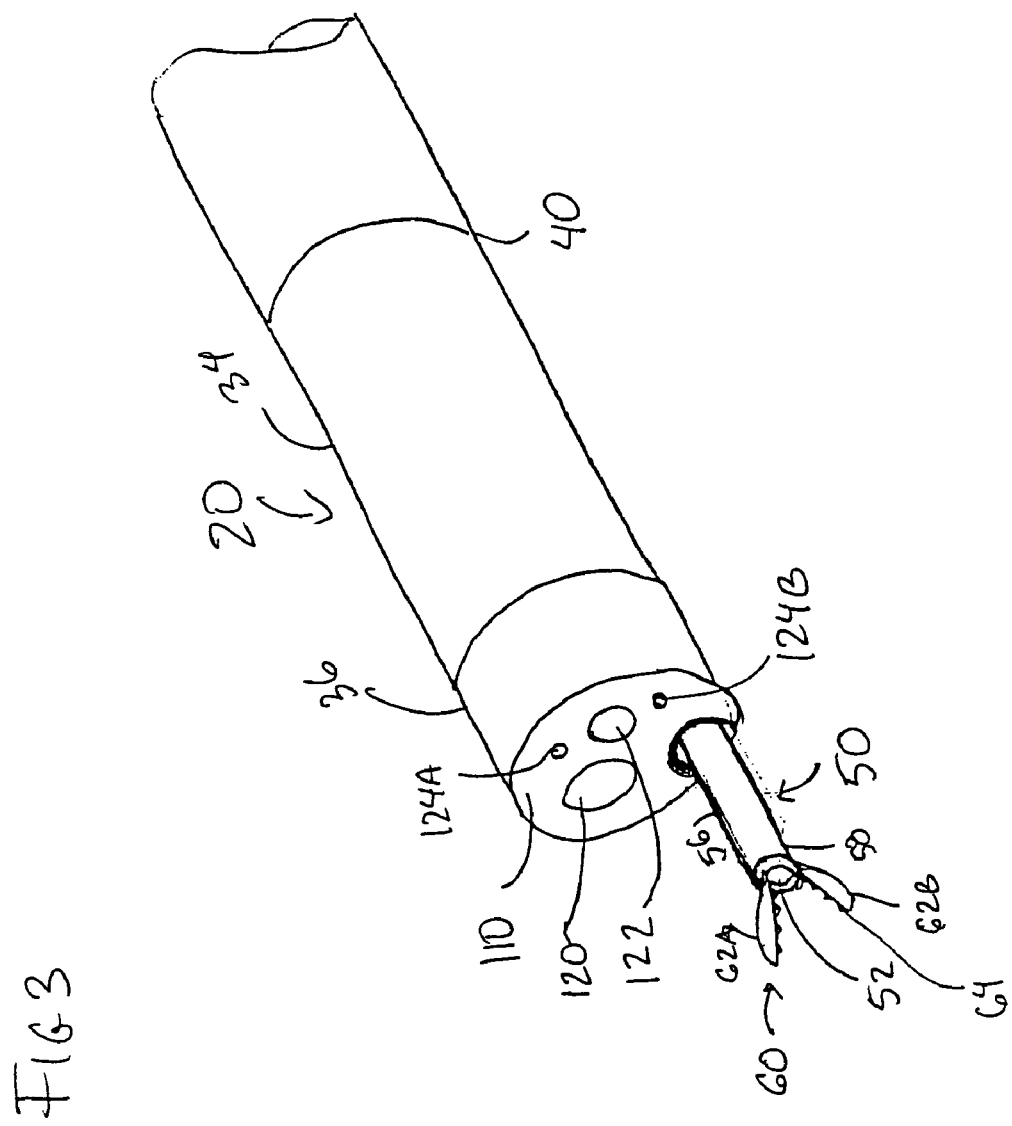

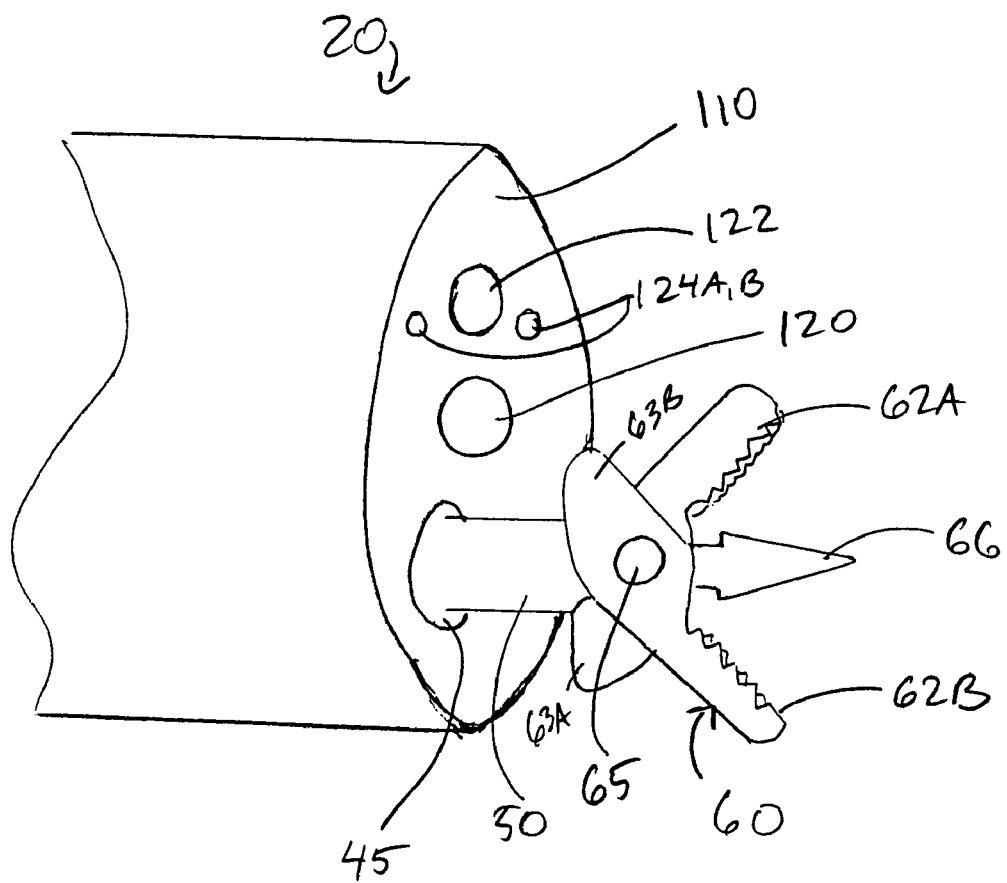

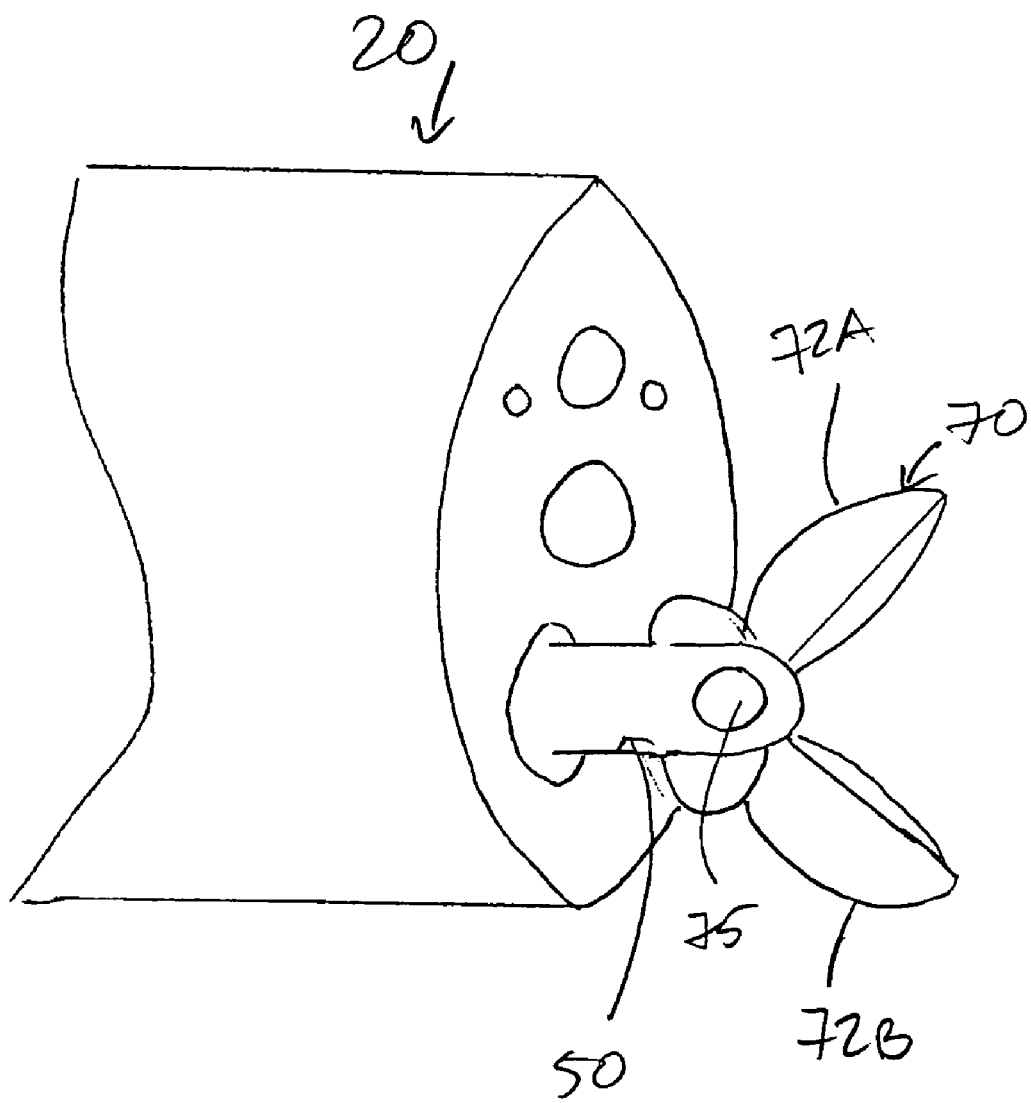

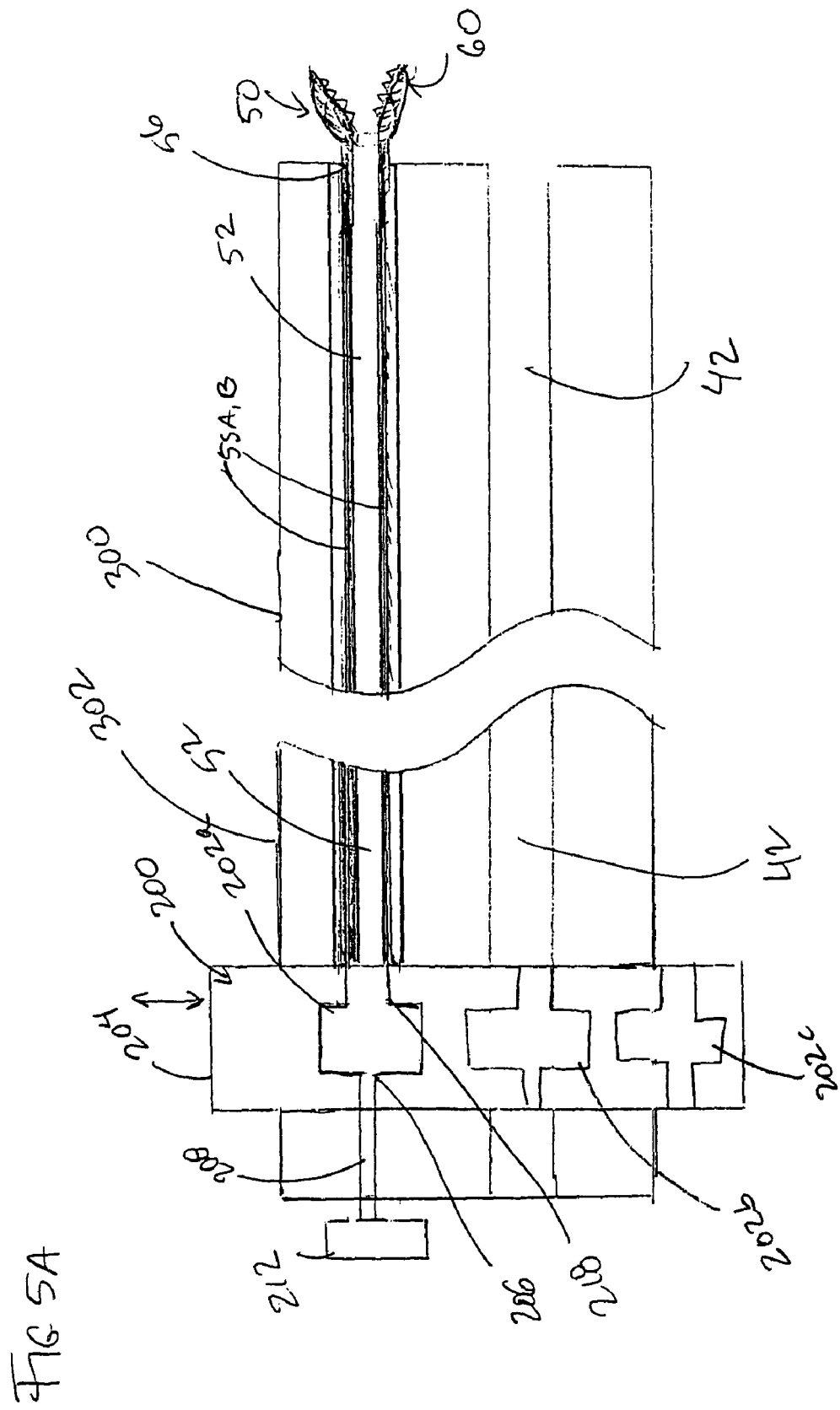

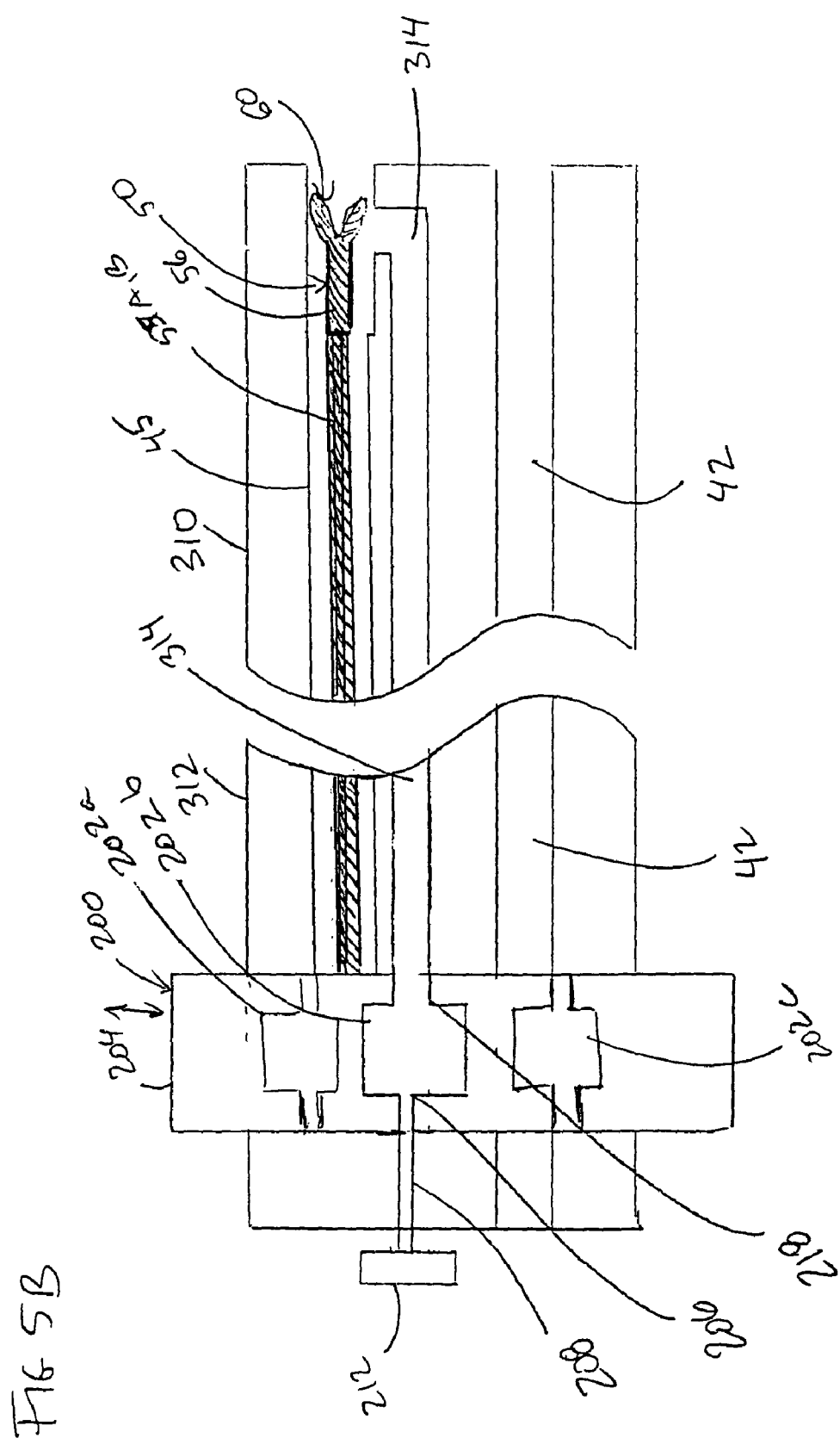

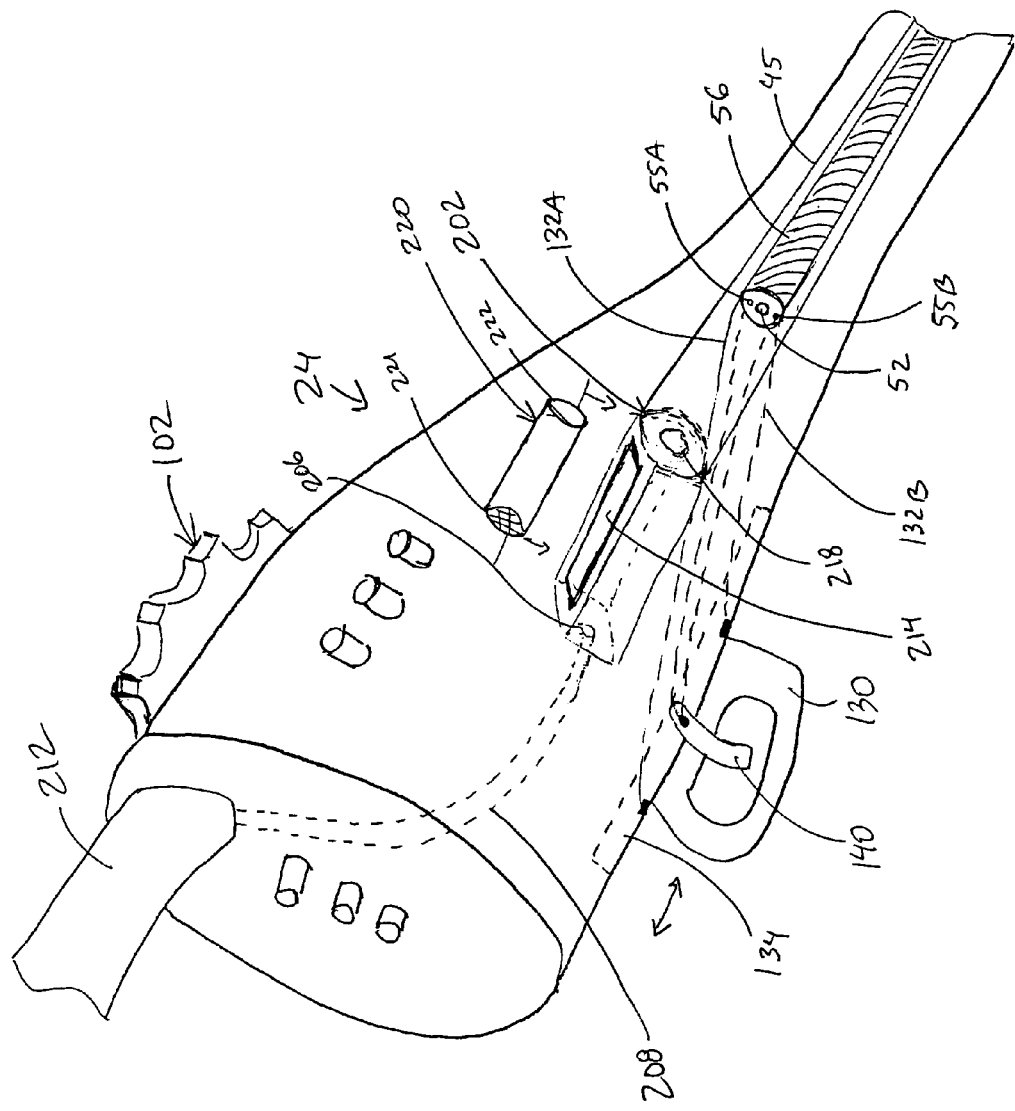

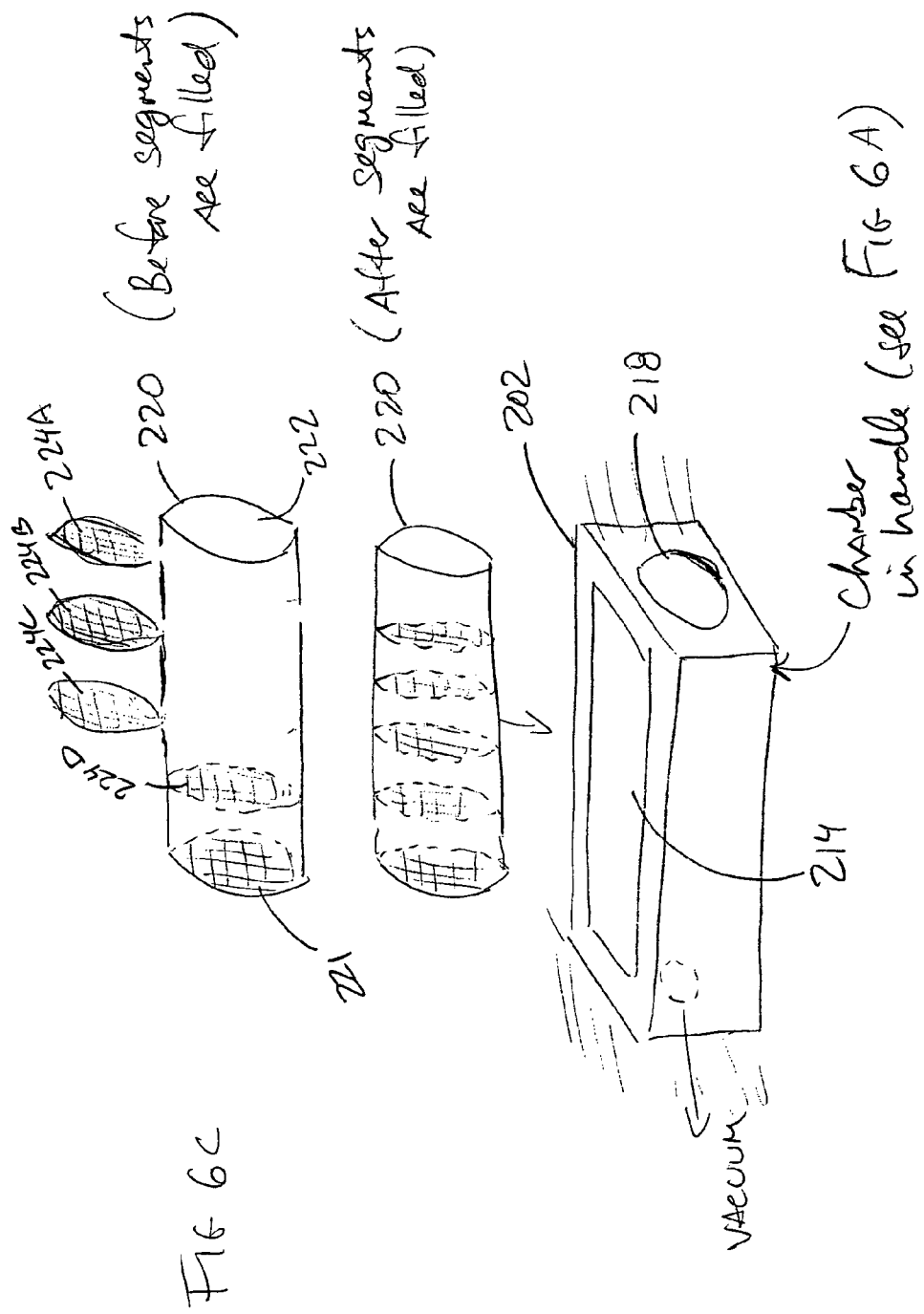

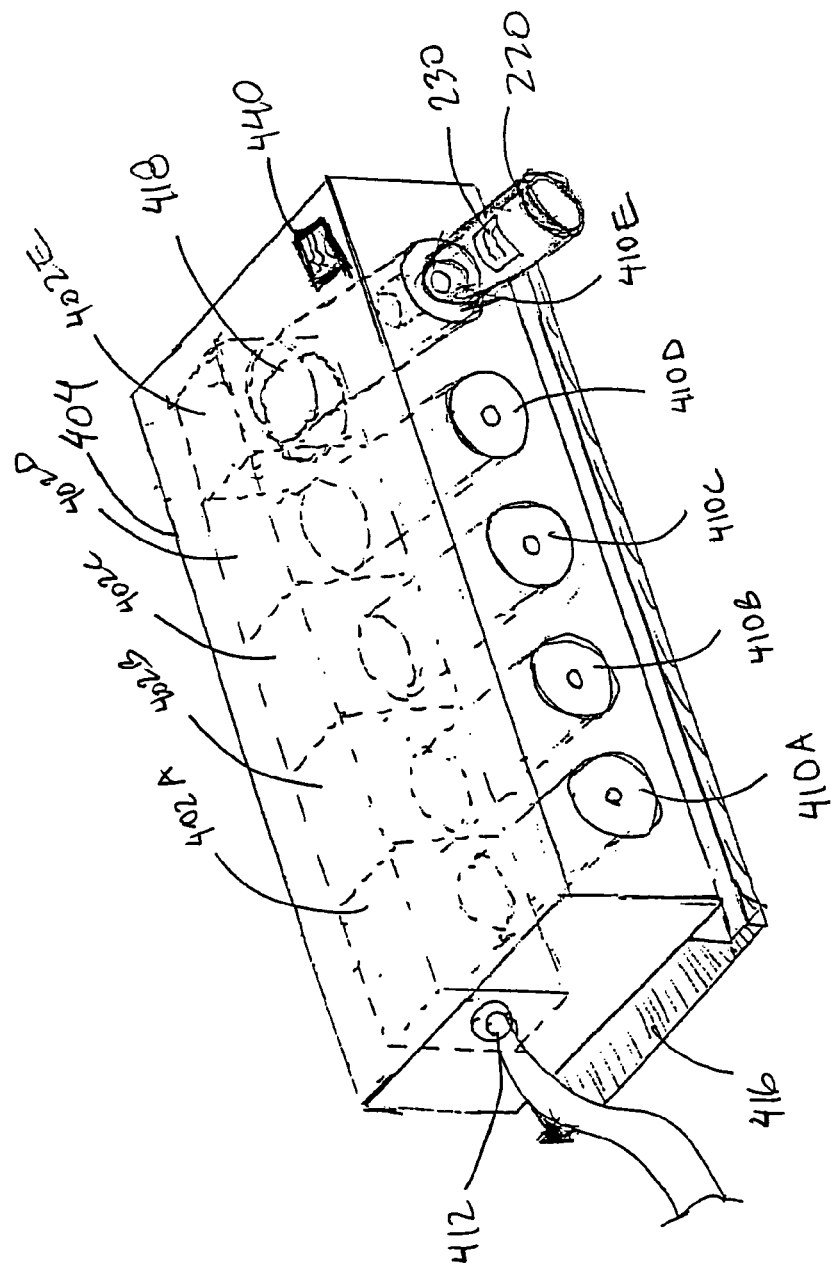

ENDOSCOPIC APPARATUS WITH INTEGRATED MULTIPLE BIOPSY DEVICE

FIELD OF THE INVENTION

The present invention relates to medical devices in general and to biopsy devices in particular.

BACKGROUND OF THE INVENTION

It has become well established that there are major health benefits from regular endoscopic examinations of a patient's internal structures such as the alimentary canals and airways, e.g., the esophagus, stomach, lungs, colon, uterus, urethra, kidney, and other organ systems. Endoscopes are also commonly used to perform surgical, therapeutic, diagnostic, or other medical procedures under direct visualization. A conventional imaging endoscope used for such procedures includes an illuminating mechanism such as a fiber optic light guide connected to a proximal source of light, and an imaging means such as an imaging light guide to carry an image to a remote camera, or eye piece, or a miniature video camera within the endoscope itself. In addition, most endoscopes include one or more working channels through which medical devices such as biopsy forceps, snares, fulgration probes, and other tools may be passed in order to perform a procedure at a desired location in the patient's body.

At the proximal end of the endoscope is a handle that includes steering controls and other actuators that allow a user to control the orientation and operation of the endoscope. The endoscope is guided through the patient's tract or canal until an opening at or adjacent the distal end of the endoscope is proximate to the area of the patient's body which is to be examined or receive treatment. At this point, the endoscope allows other tools, such as a catheter or biopsy forceps, to access the targeted area.

Conventional endoscopes are expensive, hand assembled, medical devices costing in the range of $25,000 for an endoscope, and much more for the associated operator console. Because of this expense, these conventional endoscopes are built to withstand repeated disinfections and use upon many patients. Conventional endoscopes are generally built of sturdy materials, which decreases the flexibility of the scope and thus can decrease patient comfort. Furthermore, conventional endoscopes are complex and fragile instruments that frequently need expensive repair as a result of damage during use or during a disinfection procedure.

Low cost, disposable medical devices designated for a single use have become popular for instruments that are difficult to clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. One medical device that has not previously been inexpensive enough to be considered truly disposable is the endoscope, such as a colonoscope, bronchoscope, gastroscope, duodenoscope, etc. Such a single-use or disposable endoscope is described in U.S. patent application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc., and are hereby incorporated by reference.

Biopsies are often performed using an endoscope to determine whether a tumor is malignant or to determine the cause of an unexplained inflammation. For example, a gastrointestinal biopsy is typically performed through a flexible endoscope. The endoscope is guided by an operator to the desired location in the body and a tool is inserted through a lumen to the biopsy site. While viewing the biopsy site through the optical lens of the endoscope, an operator manipulates an actuating handle to effect a tissue sampling. After a sample has been obtained, the operator then carefully withdraws the biopsy tool from the endoscope while holding the actuating handle to maintain the jaws in a closed position. The above described endoscopic biopsy procedure generally requires two or three people, including the operator controlling the endoscope, and one or more assistants to actuate the biopsy forceps, withdraw the tissue specimen, place the specimen into a sterile container with a label, and send the container to pathology for analysis.

The process of taking a biopsy presents several challenges, including accurate targeting of the biopsy site, precise and accurate penetration of the biopsy site, preservation of the biopsy tissue upon extraction, and tracking the source of the biopsy sample. Multiple biopsies are often required in order to obtain an accurate diagnosis of malignant tumors, inflammatory conditions, and infectious processes and are also used to improve the diagnostic yield of tissue for later analysis. Multiple biopsies during a single clinical procedure amplify the above-mentioned challenges.

To obtain multiple samples with a conventional biopsy system, biopsy tools must be repeatedly inserted and the sample retrieved, thereby compounding the already awkward procedure. In addition, conventional biopsy systems are not equipped with a sample retrieval device for receiving and cataloging multiple samples, and such systems do not provide a method by which the precise location of the biopsy site can be tracked and correlated with the biopsy sample.

SUMMARY OF THE INVENTION

To address these and other concerns, in one embodiment the present invention is an imaging endoscope comprising a shaft having a proximal end adapted to be secured to a handle, and a distal end with biopsy forceps disposed within the distal end. The biopsy forceps includes a shaft coupled to a bite assembly. The bite assembly includes two or more cooperating end-effector elements that are actuated with one or more control cables. The endoscope shaft includes a biopsy sample lumen that is configured to receive a biopsy sample obtained with the bite assembly. In one embodiment, the handle includes a housing that includes at least one actuator for actuating control wires connected to the biopsy forceps, and a sample collection apparatus configured to capture multiple biopsy samples obtained with the biopsy forceps. The sample collection apparatus includes one or more sample chambers each adapted to receive a sample vial. Each sample chamber includes a port for forming a connection with the biopsy sample lumen in the endoscope shaft and a vacuum inlet port configured to permit a vacuum to be selectively applied to the sample chamber. In some embodiments, the sample chamber is located within the handle. In other embodiments, one or more sample chambers are located in a cassette comprising a plurality of sample vials that is removably coupled to an attachment element on the handle.

In another embodiment, the present invention is a multiple biopsy system that includes an imaging endoscope with a biopsy forceps disposed within a distal end. At a proximal end is a handle having an actuator capable of actuating a control cable connected to the biopsy forceps apparatus. In some embodiments, the biopsy forceps is an apparatus that is separate from the endoscope and is capable of insertion into a tool lumen. In other embodiments, the biopsy forceps apparatus is an integral component of the endoscope. The handle further includes a sample collection apparatus comprising a sample chamber adapted to receive a sample vial and a removable cassette comprising a plurality of sample vials. In some embodiments, the system further comprises a control unit having a tracking system that records coordinates corresponding to each biopsy sample. In additional embodiments, the control unit further includes a digital monitor, graphical user interface, and multiplexer so that biopsy information can be multiplexed onto the display and/or recorded for labeling each biopsy sample.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a cross-sectional view of an endoscope shaft formed in accordance

FIG. 3 illustrates a representative embodiment of biopsy forceps disposed within the distal end of an imaging endoscope in accordance with an embodiment of the present invention;

FIG. 4A illustrates an embodiment of a bite assembly on biopsy forceps disposed within the distal end of an imaging endoscope in accordance with an embodiment of the present invention;

FIG. 4B illustrates another embodiment of a bite assembly on biopsy forceps disposed within the distal end of an imaging endoscope in accordance with an embodiment of the present invention;

FIG. 5A is a partial cut-away view of an embodiment of an endoscope shaft connected to a handle in accordance with an embodiment of the present invention;

FIG. 5B is a partial cut-away view of another embodiment of an endoscope shaft connected to a handle in accordance with an embodiment of the present invention;

FIG. 6A is a partial cut-away view of a handle comprising a sample chamber for retrieving a biopsy sample in accordance with an embodiment of the present invention;

FIG. 6C is a partial cut-away view of an embodiment of a sample collection vial;

FIG. 7 is a perspective view of an exemplary embodiment of a sample vial cassette in accordance with an embodiment of the present invention;

DETAILED DESCRIPTION OF THE PREFERRED EMBODIMENT

To address the problems associated with obtaining multiple biopsy samples using conventional endoscope systems and others, the present invention is an imaging endoscope having an elongated shaft with a proximal and distal end with biopsy forceps capable of taking multiple biopsy samples disposed within the distal end. The present invention provides many advantages over conventional endoscope systems and biopsy devices. For example, the present invention provides ease of use such that a single operator may obtain multiple biopsy samples without withdrawing the endoscope or the biopsy tool. Other advantages include, but are not limited to, the ability to capture a plurality of biopsy samples into individual sterile containers, the ability to map the location coordinates of the biopsy site, and the use of a programmable firing mechanism for obtaining precise and high quality tissue samples.

The various embodiments of the endoscope described herein may be used with both reusable and low cost, disposable endoscopes, such as an endoscope that is sufficiently inexpensive to manufacture such that it can be a single-use device as described in U.S. patent application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc, and are hereby incorporated by reference.

While the invention is described in terms of a multiple biopsy system and apparatus, it will be understood by one of skill in the art that the endoscope having the integrated biopsy apparatus is a multifunctional device that may also be used for a variety of different diagnostic and interventional procedures, including colonoscopy, upper endoscopy, bronchoscopy, thoracoscopy, laparoscopy, and video endoscopy, etc., in addition to multiple biopsy.

Figure 1:
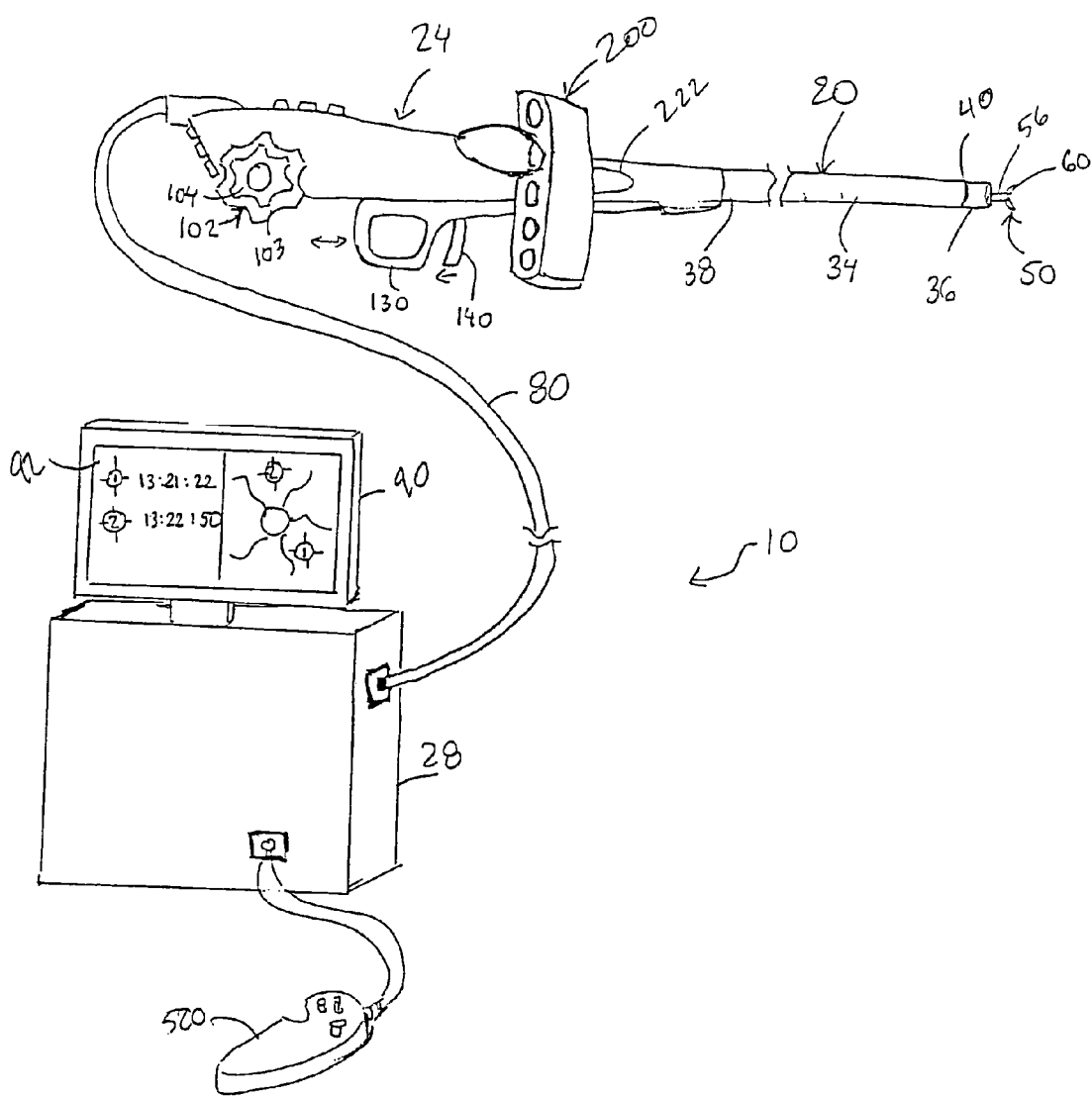
FIG. 1 is a diagram illustrating a multiple biopsy system in accordance with one embodiment of the present invention.

FIG. 1 illustrates the major components of an endoscopic multiple biopsy system 10 according to an embodiment of the present invention. The components of the system 10 include an imaging endoscope 20 comprising an elongated shaft 34 having a distal end 36 and a proximal end 38. The distal end 36 includes an imaging system and the proximal end 38 is connected to a handle 24. The endoscope 20 is functionally connected and controlled by the handle 24, which is, in turn, connected to a control unit 28 via a conduit 80. The control unit 28 functions to provide image processing capabilities for image display on a display monitor 90, as well as a supply of power, fluids, vacuum, and the like to the endoscope 20. A user input device 500, such as a joystick, keyboard or the like allows an operator to input patient data and control the operation of the control unit 28. The endoscope 20 further includes a biopsy forceps 50 that is disposed within the endoscope shaft 34 and is extendable beyond the distal end 36 of the endoscope 20. The biopsy forceps 50 comprises a shaft 56 and a bite assembly 60 that is actuated by an actuator on the handle 24. Tissue samples obtained with the bite assembly 60 are retrieved through a biopsy sample lumen 52 (shown in FIG. 2) and placed in a collection apparatus 200 as described in more detail below. In some embodiments, the biopsy forceps 50 is a separate instrument that is insertable into a lumen in the endoscope 20. In other embodiments, the biopsy forceps 50 is integrally formed with the endoscope 20.

The endoscope 20 can be any single-use or reusable, flexible, partially-flexible, or rigid elongated probe such as, for example, a bronchoscope or a colonoscope. In the embodiment shown in FIG. 1, the endoscope includes an articulation joint 40 proximal to the distal end to provide sufficient flexibility to the distal end 36 of the shaft 34 such that the distal end 36 can be directed over a required deflection range (e.g., 180° or more). The endoscope 20 has a set of control cables, shown best in FIG. 2, that control the motion of the distal end 36. The distal ends of the control cables are attached at, or adjacent to the distal end 36 of the shaft, while the proximal ends of the control cables are attached to actuators in the handle 24.

FIG. 2 is a cross-sectional view of an embodiment of the elongated shaft 34 of the endoscope 20. The endoscope shaft 34 includes a working channel or lumen(s) 42 for the purpose of performing endoscopic procedures and for the purpose of facilitating the delivery or extraction of fluids, gases, and/or medical devices into and out of the body. Also included in the shaft 34 is a biopsy sample lumen 52 that has a distal end that is functionally connected to, or integrally formed with, the biopsy forceps 50 at the distal end 36 of the endoscope 20. The biopsy sample lumen 52 has a proximal end that is functionally connected to the biopsy sample collection apparatus 200. In the embodiment of the endoscope shaft 34 shown in FIG. 2, the biopsy sample lumen 52 is disposed within the biopsy forceps shaft 56, which in turn is disposed within a tool lumen 45. The forceps shaft 56 contains two control cables 55A and 55B that control the bite assembly 60 of the biopsy forceps 50. With continued reference to FIG. 2, the endoscope shaft 34 also includes one or more electrical wires 44, 46 that extend from the distal end 36 of the endoscope to the handle 24 for supplying power to illumination LEDs in the distal end 36 and to transmit images from an image sensor (not shown) in the distal end 36 back to the control unit 28, respectively.

With continued reference to FIG. 2, the shaft 34 also includes at least one pair of control cables 47A, 47B, and preferably two pairs of control cables 47A, 47B and 48A, 48B, that are connected at, or adjacent to, the distal end 36 of the shaft and are actuated to control the distal end 36 of the shaft 34. As best shown in FIG. 1, the handle 24 contains a manually actuated steering mechanism 102 for effecting 4-way steering of the distal end 36 in the up/down and right/left directions. This mechanism 102 includes an inner knob 104 to control up/down steering and an outer knob 103 to control right/left steering. The knobs 103 and 104 are connected to the proximal ends of the control cables 47A, 47B and 48A, 48B, respectively (see FIG. 2), that extend through the endoscope shaft 34 so that rotation of the knobs selectively tightens or relaxes the control cables in order to bend the distal end 36.

In some embodiments, the endoscope 20 may contain a breakout box (not shown) that is positioned midway along the length of the shaft 34 and provides an entrance to the working channel 42 or tool lumen 45 so that additional medical devices such as forceps, snares, fulguration probes, and other tools may be passed through the breakout box and into the working channel 42 or tool lumen 45.

FIG. 3 illustrates a representative embodiment of the endoscope 20 and shows more detail of the biopsy forceps 50 disposed within the distal end 36 of the endoscope 20. As shown in FIG. 3, fitted onto the distal end 36 of the shaft 34 is a distal end cap 110 having a number of ports and the biopsy forceps 50 extending distally beyond the distal end cap 110. The biopsy forceps 50 comprises a shaft 56 having a distal end 58 and a proximal end that is disposed within the tool lumen 45 in the endoscope shaft 34 (hidden in FIG. 3). The biopsy shaft 56 is actuated by a ring 130 that is slidably engaged on the endoscope handle 24 (shown best in FIG. 6A) and is capable of a limited range of back and forth movement within the tool lumen 45. The tool lumen 45 is sized at its distal end so that the biopsy forceps 50 may be retracted into the distal end 36 of the endoscope shaft 34. In the embodiment shown in FIG. 3, the shaft 56 of the biopsy forceps 50 is hollow, and the sample biopsy lumen 52 extends through the hollow shaft 56.

With continued reference to FIG. 3, the biopsy forceps 50 further includes the bite assembly 60 having two or more cooperating end-effector elements 62A and 62B that are pivotably connected at the distal end of the shaft 56. In the embodiment of the forceps shaft 56 shown in FIG. 3, the end-effector elements 62A and 62B are located at positions adjacent to the sample biopsy lumen 52 such that a biopsy sample cut from a body by the end-effector elements 62A, 62B is pulled into the lumen 52 of the biopsy forceps 50 by a vacuum, or some other method.

The end-effector elements 62A and 62B may be in the form of various shapes that are capable of being actuated (e.g., fired) in a repetitive manner in order to obtain a plurality of individual tissue biopsy samples. For example, the end effector elements 62A and 62B may comprise jaws that are shaped into various forms, such as flat or cupped jaws that comprise teeth along their cutting edge to sever and retain a biopsy sample, such as those described in U.S. Pat. Nos. 5,507,296, and 5,666,965, both of which are hereby incorporated by reference. In another example, the end-effector elements 62A and 62B may be shaped into two substantially parallel tangs, one being shorter than the other, as described in U.S. Pat. No. 5,707,392, which is hereby incorporated by reference. In the embodiment of the endoscope 20 shown in FIG. 3, the bite assembly 60 comprises a pair of end-effector elements 62A and 62B in the form of movable cutting jaws. Each jaw 62A, 62B is generally elongated having a hemispherically shaped with an array of teeth 64 disposed along the rim of each jaw 62A and 62B such that closure of the jaws cuts a tissue sample.

FIG. 4A shows another embodiment of a biopsy forceps 50 disposed within the tool lumen 45. The biopsy forceps 50 includes a bite assembly 60 with a cutting blade 66 disposed between the two cutting jaws 62A and 62B. The cutting blade 66 may be located adjacent to the biopsy sample lumen 52 in the forceps shaft 56, or alternatively, the biopsy sample lumen 52 may connect to a hole through the blade 66. The cutting jaws 62A and 62B are levered about a clevis pin 65 which extends through a bore on each respective jaw. The distal end of each jaw 62A, 62B has cutting teeth and the proximal end of each jaw terminates in a pair of tangs 63A, 63B. The control cables 55A and 55B (shown in FIG. 2) are each connected at or adjacent to a tang 63A, 63B of each jaw 62A, 62B so that an actuator tensioning the control cables 55A, 55B engages the distal end 62A, 62B of the jaws to mate together in a cooperative biting action. In one embodiment, the control cables 55A, 55B terminate in the handle 24, and are actuated by a trigger 140 (shown best in FIG. 6B) as further described below.

Also included at the distal end cap 110 of the endoscope 20 is an imaging port 122 that houses an imaging system (not shown) and illumination ports 124A, 124B containing illumination port lenses (not shown). Further included on the distal end cap 110 is an access port 120 that defines the entrance to the working channel lumen 42. The imaging system in the endoscope 20 can be of the optical type (i.e., fiberscope) in which an optical image is carried on a coherent fiber optic bundle to a remote eyepiece or camera. Alternatively, the imaging system can include a distal imaging sensor or a miniature camera, which includes a charge coupled device (CCD) or CMOS imaging sensor. In one embodiment, the endoscope 20 includes a CMOS image sensor, plastic optics, and LED illumination as further described in U.S. patent application Ser. No. 10/811,781, filed Mar. 29, 2004, and in a U.S. Continuation-in-Part patent application Ser. No. 10/956,007, as discussed above.

FIG. 4B shows another embodiment of the distal end of the endoscope 20 with a forceps assembly 70 having end-effector elements levered about a clevis pin 75 in the form of a pair of cup-shaped cutting jaws 72A and 72B which may additionally include cutting teeth (not shown).

Returning again to FIG. 1, as mentioned above, the proximal end 38 of the endoscope shaft 34 is disposed in the handle 24. The handle 24 is also coupled to the control unit 28 with a flexible shaft through which a conduit 80 passes. In an embodiment of the system 10, the conduit 80 functionally interconnects the handle 24 to the control unit 28. The conduit 80 carries image information back to the imaging electronics housed in the control unit 28 from the imaging sensor in the distal end 36 of the endoscope 20. The shaft between the control unit 28 and the handle 24 further carries power for the illumination LEDs, as well as carrying irrigation/insufflation fluids through the shaft 34 to the distal end 36 of the endoscope 20. In one embodiment of the system 10, vacuum pressure is provided through the shaft to a manifold (not shown) in the handle 24 that, in turn, selectively applies vacuum pressure to the working channel 42 and/or to a port connected to the sample collection apparatus 200 in order to suction biopsy samples into the biopsy sample collection apparatus 200 from the biopsy sample lumen 52, as further described below.

FIG. 5A shows a partial cut away of a simplified view of one embodiment of an endoscope shaft 300 connected to a handle 302. The endoscope shaft 300 includes the working channel 42 and the biopsy forceps 50 disposed in the tool lumen 45. The biopsy forceps 50 has a hollow shaft 56, wherein the hollow shaft 56 defines a passage between the jaws of the end-effector elements on the bite assembly 60. A removable sample vial cassette 204 includes multiple sample chambers 202a, 202b, and 202c which receive a corresponding set of sample vials (not shown). The proximal end of the biopsy sample lumen 52 is connected to an inlet port 218 in the sample chamber 202a. A vacuum outlet port 206 leads from the sample chamber 202a to a vacuum line 208 that is, in turn, connected to a vacuum source 212 that is selectively applied by a user and may be contained within the control unit 28. The sample vial cassette 204 may hold from 4 or fewer sample vials up to 10 or more sample vials.

In operation of the endoscope 300 shown in FIG. 5A, the removable cassette 204 is positioned so that the sample vial in the sample chamber 202a is aligned with the proximal end of the biopsy lumen 52. The bite assembly 60 is actuated by a trigger 140 (shown in FIG. 1 and FIG. 6B) on the handle 302 to obtain a biopsy sample, as described in more detail below. A vacuum is selectively applied via the vacuum line 208, thereby pulling the biopsy sample through the biopsy sample lumen 52 in the hollow shaft 56 into the sample vial (not shown) positioned in the sample chamber 202a. Fluid may also be supplied to the sample chamber to allow sample preservation and ease of sample manipulation. The sample vial may then be sealed to maintain the integrity of the sample, and the cassette 204 is moved to a new position corresponding to an empty sample vial in another sample chamber (202b, 202c, etc.) Once the sample vials in the cassette 204 are filled, the cassette is removed from the handle 302 and replaced with another cassette filled with empty vials.

FIG. 5B shows another embodiment of an endoscope shaft 310 connected to a handle 312. The endoscope shaft 310 comprises the working channel 42 and the biopsy forceps 50 disposed within the tool lumen 45. In accordance with this embodiment, the biopsy forceps 50 may be a separate instrument from the endoscope 310 and may be inserted into the tool lumen 45 via the breakout box, described above. The biopsy forceps shaft 56 is retractable into a distal portion of the tool lumen 45. A separate sample biopsy lumen 314 is in fluid communication with the distal portion of the tool lumen 45, such that vacuum may be selectively applied to the sample biopsy lumen 314 via the vacuum line 208. The proximal end of the sample biopsy lumen 314 is in fluid communication with the sample chamber 202b in the sample cassette 204. In operation of the endoscope 310, the removable cassette 204 is positioned so that a sample vial in the sample chamber 202b is aligned with the proximal end of the sample biopsy lumen 314. The bite assembly 60 on the biopsy forceps 50 is actuated by the trigger 140 on the handle 24 to obtain a biopsy sample. The bite assembly 60 holding the biopsy sample is then retracted into the distal portion of the lumen 45 through the use of the ring 130 on the handle 312. Vacuum is selectively applied via the vacuum line 208, thereby pulling the biopsy sample through the sample biopsy lumen 314 into the sample vial positioned in the sample chamber 202b. The sample vial may then be sealed, and the cassette 204 is moved to a new position corresponding to an empty sample vial in the adjacent sample chamber 202c, as described above.

FIG. 6A shows more detail of an embodiment of the handle 24 connected to the proximal end of the endoscope 20. As mentioned above, the forceps shaft 56 is movably disposed within the tool lumen 45. In the embodiment of the handle 24 shown in FIG. 6A, the biopsy sample lumen 52 is disposed within the forceps shaft 56. A pair of control cables 132A, 132B are attached at or adjacent to the proximal end of the forceps shaft 56 of the biopsy forceps 50. The control cables 132A, 132B are actuated by the ring 130 that is slidably engaged in a track 134 on the handle 24. To orient the biopsy forceps 50 in a desired position, an operator pulls the cables 132A and 132B to retract the forceps shaft 56 by moving the ring 130 to a proximal position in the track 134. Conversely, the forceps shaft 56 may be advanced beyond the distal end cap 110 of the endoscope 20 by moving the ring 130 to a distal location in the track 134.

As mentioned above in reference to FIG. 4A, each control cable 55A and 55B is coupled at its distal end to the corresponding end-effector element 62A and 62B (see FIG. 4A) and extends proximally through the endoscope shaft 34 to terminate at the handle 24 where it is actuated by a user input device, such as the trigger 140. In operation, proximal movement of the trigger 140 effectuates a tension force on the control cables 55A and 55B so as to create a pivotable cooperative cutting motion of the end-effector elements 62A and 62B, such that the elements 62A and 62B engage each other. Conversely, movement of the trigger 140 distally effectuates a compression of the control cables 55A and 55B so as to open the end-effector elements 62A and 62B. In some embodiments of the system 10, the trigger 140 provides manual control over the end-effector elements 62A and 62B in the forceps assembly 60. In other embodiments of the system 10, the trigger 140, or other input device that causes the activation of the biopsy forceps, provides an input signal that is actuated (e.g., fired) with a preprogrammed force. The preprogrammed force may be provided by a spring (not shown), pneumatic device, hydraulic, electromotive or other driver mechanism included in the handle 24. While the actuators have been described in terms of rings and triggers, it will be understood by one of skill in the art that other types of controls are possible, such as rotating controls, motor driven, hydraulic, pneumatic controls and the like are also possible.

As further shown in FIG. 6A, the sample chamber 202 is included within the handle 24. The sample chamber 202 includes the inlet port 218 that is in selective fluid communication with the sample retrieval lumen 52, an opening 214 sized to receive a sample vial 220, and a vacuum port 206 attached to a vacuum line 212. The sample vial 220 has a first end 222 with an opening adapted to capture a biopsy sample, and a second end 221 adapted to allow the application of a vacuum pressure through the sample vial, while still retaining the captured biopsy sample, such as, for example, a screen, filter, or other suitable equivalent. As shown in FIG. 6C, in one embodiment, the sample vial 220 has a segmented structure, wherein a series of dividers, such as screens 224A, 224B, 224C and 224D are inserted into position as biopsy samples are collected into each respective segment. The dividers may be inserted by the user, or alternatively, an actuator may be provided in the handle that moves the dividers into position in the sample vial between each sample capture.

Figure 6B:
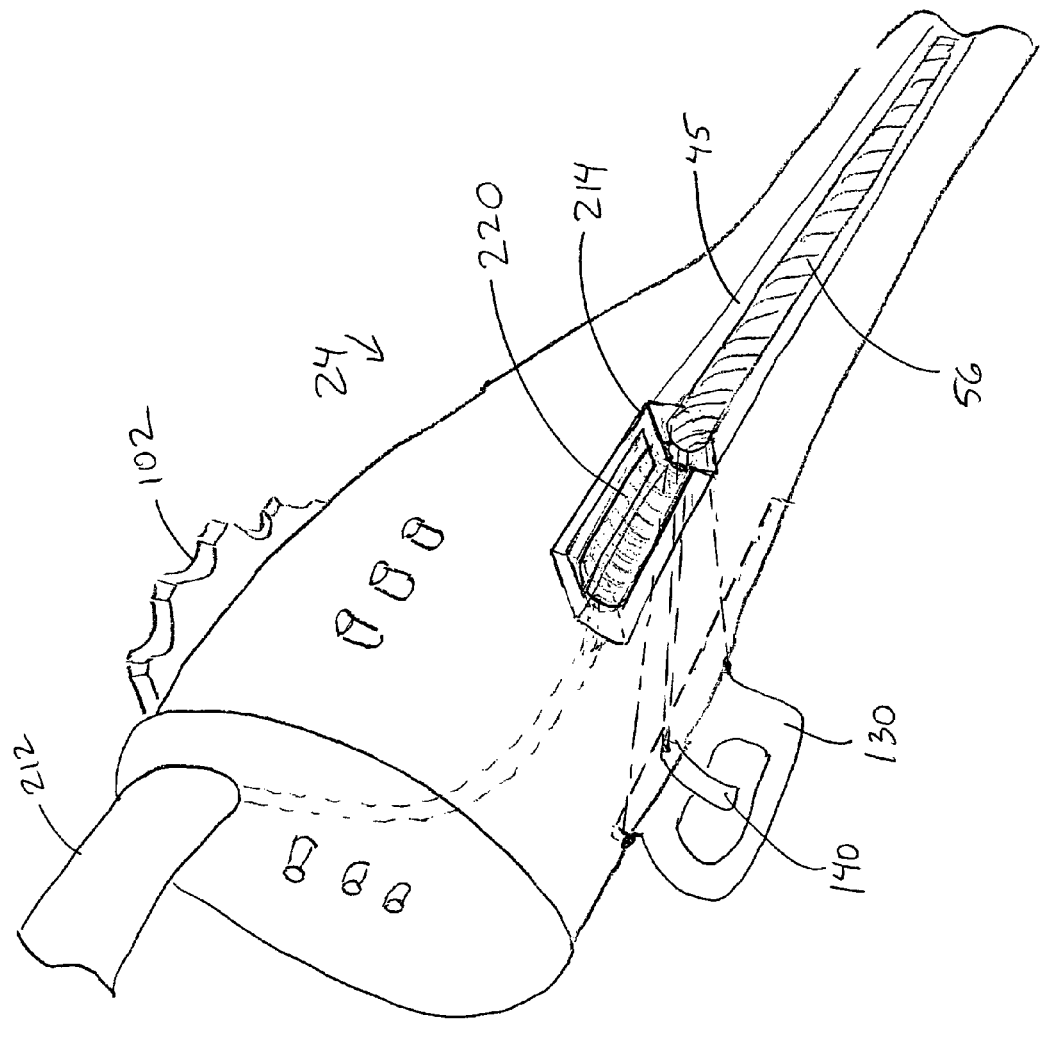
FIG. 6B is a partial cut-away view of the handle shown in FIG. 6A, illustrating a sample retrieval lumen positioned adjacent a sample collection chamber.

In operation, the end-effector elements 62A, 62B are actuated by a user with the trigger 140 to obtain a biopsy sample. The user then slides the ring 130 to a proximal position to position the proximal end of the biopsy sample lumen 52 adjacent to the inlet port 218 on the sample chamber 202 as shown in FIG. 6B. The sample vial 220 is disposed into the opening 214 of the sample chamber 202, (as shown in FIG. 6B) and a vacuum is selectively applied through the vacuum port 208 to capture the biopsy sample from the biopsy sample lumen 52.

In some embodiments, the biopsy sample is retrieved by flushing the sample through the biopsy sample lumen 52 with air and/or water or other liquid supplied from the distal end of the endoscope shaft 34. In such embodiments, an additional lumen that carries the air/water is included in the endoscope shaft 34 and the air/water is supplied from the handle 24, or the control unit 28, or another external source. In some embodiments, the interior walls of the biopsy sample lumen 52 is coated with a hydrophilic lubricious coating to facilitate biopsy sample retrieval.

FIG. 7 shows an embodiment of the sample collection apparatus in the form of a sample vial cassette 404 that is removably secured to the handle 24. The sample vial cassette 404 comprises one or more sample chambers, shown as 402A, 402B, 402C, 402D, and 402E. Each sample chamber 402A, 402B, etc., has an inlet port 418 for connection to the biopsy sample lumen 52, a vacuum port (not shown) in selective fluid communication with the vacuum line 412, and an opening 410A, 410B, 410C, 410D, and 410E adapted to receive a sample vial 220. As shown in FIG. 7, the sample vial 220 is inserted into the opening 410E.

The sample vial cassette 404 is removably secured to the handle 24 with an attachment element 416 and is moved either manually or automatically into position so each sample vial 220 is placed into the sample chamber in line with the biopsy sample lumen 42 and vacuum source to capture a biopsy sample. Once the sample vials are filled, a new cassette 404 may be utilized, or alternatively, the sample vials may be removed and replaced with new vials. Therefore, through the use of the system 10, multiple tissue biopsies samples may be obtained during a single clinical procedure without removing the endoscope 20 and forceps apparatus 50 from the patient.

The sample vial 220 may include an identifier 230 that is preferably a unique identifier, such as a bar code, RFID tag, etc., for biopsy sample tracking. The sample identifier 230 is preferably permanently associated with the sample vial by adhesive label, etching, etc., for tracking through the pathology analysis. The cassette 404 may also include a label 440 including an identifier code that identifies a particular patient, date on which the samples were obtained or other information useful in the processing of tissue samples.

Figure 8A:
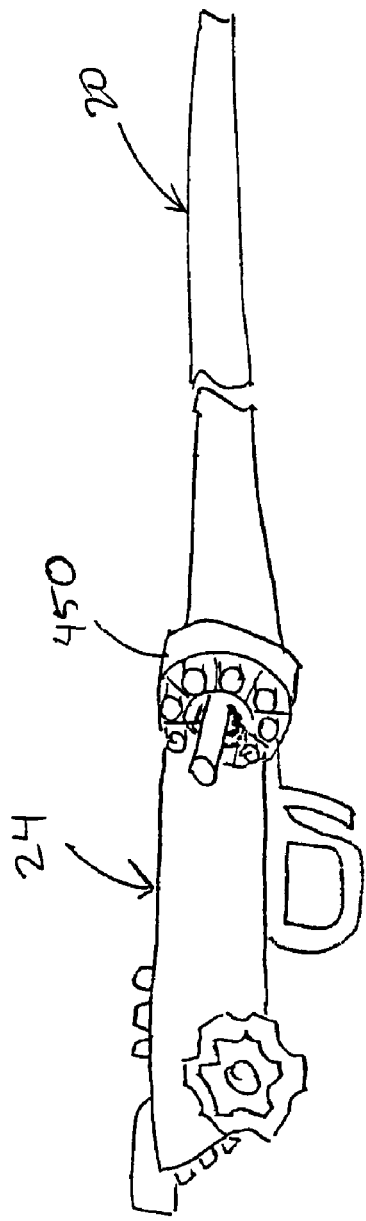
FIG. 8A is a perspective view of an embodiment of a handle comprising a circular sample vial cassette in accordance with an embodiment of the present invention.
Figure 8B:
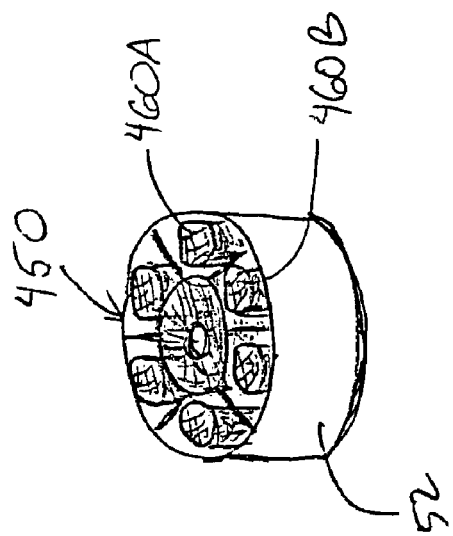
FIG. 8B is a detailed view of the embodiment of the sample vial cassette shown in FIG. 8A.

The cassette 404 may be formed into a variety of shapes, such as a rectangular shape, circular shape, and the like. An exemplary embodiment of a sample vial cassette 450 in a circular shape is shown in FIGS. 8A and 8B. As shown in FIG. 8B, the sample vial cassette 450 includes a housing 452 in a substantially cylindrical shape having a plurality of sample vials 460A, 460B, etc., disposed around the periphery of the housing 452. The cassette 450 may include from 4 or fewer sample vials to 10 or more. In use, the cassette 450 is rotated to position a new sample vial within the handle in order to receive a biopsy sample.

Figure 9:
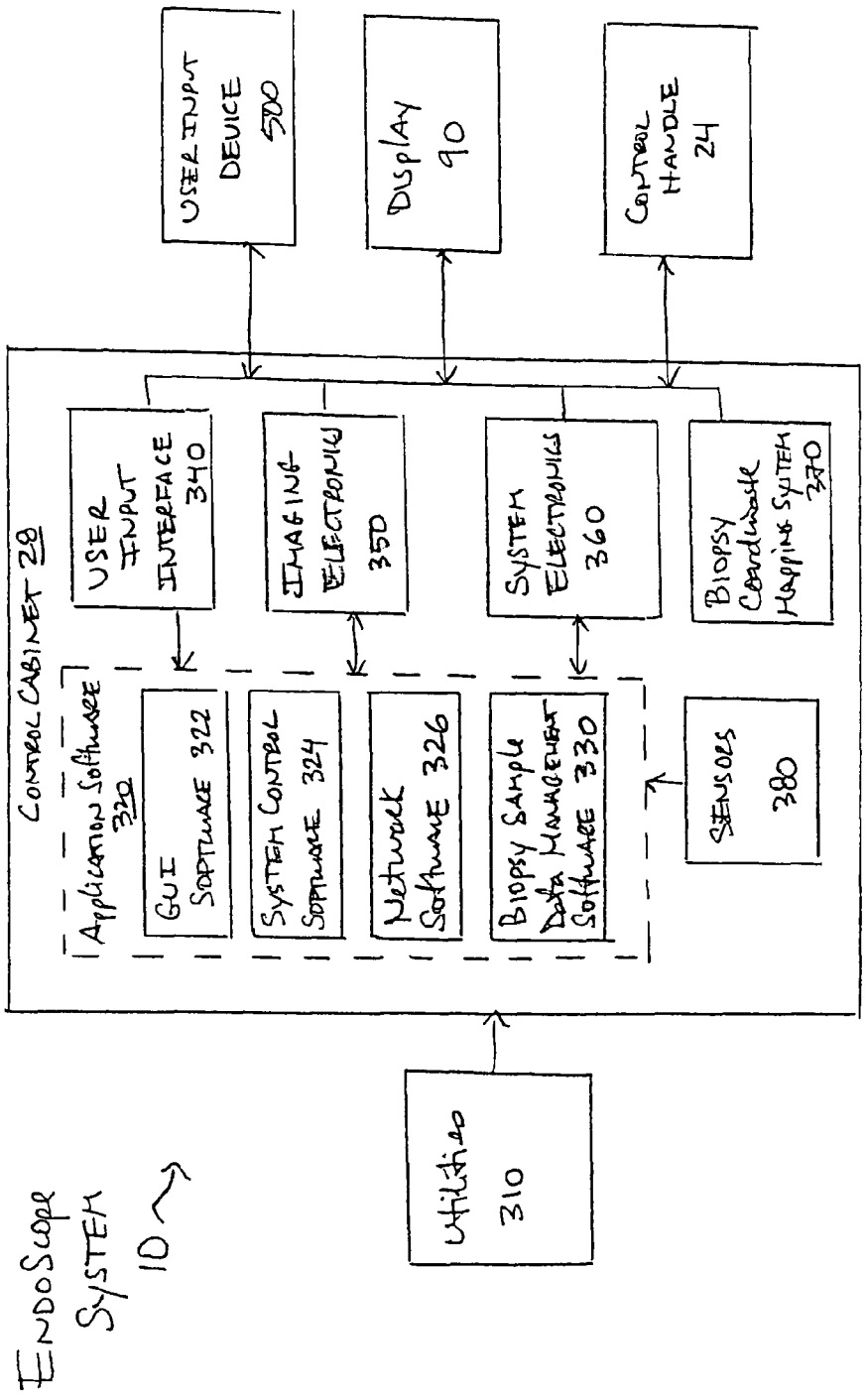
FIG. 9 is a block diagram of one embodiment of a control unit for use with the endoscope system of FIG. 1 formed in accordance with aspects of the present invention.

FIG. 9 is a block diagram of one exemplary embodiment of the control unit 28 for use in the system 10. The control unit 28 is connected to a source of electrical power, as well as to a plurality of utilities 310, including, for example, an irrigation source, an aeration source, and a source of vacuum. The control unit 28 further includes a processor (not shown), a suite of application software 320, and one or more sensors 380. The application software 320 includes a graphical user interface (GUI) software application 322, a system control software application 324, a network software application 326, and a biopsy sample data management application 330. The control unit 28 further includes an imaging electronics board 350, system electronics 360, and may additionally include a biopsy coordinate mapping system 370. The GUI software application 322 is connected to the user input device 500 via a user input interface 340.

The coordinate mapping system 370 includes means for mapping the coordinates in the body from which a biopsy tissue sample was obtained. In some embodiments, the mapping system 370 includes a coded sensor element, such as an embedded tag, for example, an RFID tag that is deployed into the tissue adjacent to the biopsy site. The position coordinates of the biopsy site may also be obtained using imaging methods such as x-ray or ultrasound technologies that are well known to those of skill in the art. In some embodiments, one or more elements of the biopsy forceps 50 include echogenic markings to improve detection with an ultrasound device. In use, the user may read the position coordinates of the biopsy site just prior to, during, or just after the biopsy is obtained and manually enter the coordinates into the control unit with the input device 500. In other embodiments, the endoscope 20 further includes a position sensor receiver element (not shown) that is tracked by a tracking system using electromagnetic radiation transmitted by two or more external antenna. For example, an electromagnetic sensor element and antenna as described in U.S. Pat. No. 6,593,884 may be used, which is hereby incorporated by reference. In such embodiments, the position coordinates may be automatically recorded in a memory within the control unit 28 and associated in a relational database with the biopsy sample vial identifier 230 via the execution of the biopsy sample management software 330.

In the diagnosis and treatment of conditions, such as malignant tumors, inflammatory conditions, and infectious processes, it is advantageous to observe a lesion over time to determine if the lesion has changed in morphology, thereby requiring an additional biopsy. Accordingly, in some embodiments, the present invention provides GUI navigational controls to allow a user to determine the status of one or more operating parameters of the system 10, such as, for example, the image and location coordinates of the biopsy tissue before a sample is obtained and after the sample has been collected.

System control software applications 324 is the central control program of application software 320 that receives input from the sensors 380 and the handle 24 provides system software control for all features and functions necessary to operate the biopsy sample system 10. In some embodiments, the system control software 324 includes preprogrammed firing modes for actuating the biopsy forceps apparatus 50. Sensors 380 may include, for example, pressure transmitters, temperature sensors, and location sensors, and are used for real-time electronic feedback of hardware operating parameters and position parameters. In some embodiments, the system 10 also may include an optical sensor for capturing an object identifier on a sample vial and/or the sample vial cassette. As each biopsy sample is collected, information related to the sample is entered via a user input device and/or captured automatically and recorded in the control unit 28, including the sample vial identifier 230, the cassette identifier 240, the location coordinates corresponding to the sample, instructions for analysis, images, and the like, using the biopsy sample data management applications 330 in the control unit 28. As shown in FIG. 1, the information related to the sample, such as location coordinates, may be displayed on a graphical user interface 92 on the digital monitor 90 along with a real-time image of the tissue at the biopsy site. The information may be downloaded to a database in a memory device, printed, and may be sent via a network interface to a remote location such as pathology lab.

While the preferred embodiment of the invention has been illustrated and described, it will be appreciated that various changes can be made therein without departing from the scope of the invention.

The embodiments of the invention in which an exclusive property or privilege is claimed are defined as follows:

1. A multiple biopsy system comprising:
    an endoscope comprising:
        an elongated shaft;
        an imaging system at or adjacent a distal end of the elongated shaft;
        a biopsy forceps disposed within the elongated shaft and having a proximal end, a shaft, and a distal end, wherein the biopsy forceps includes a bite assembly that is movable to obtain a biopsy sample;
        a handle permanently fixed and stationary relative to the elongated shaft, the handle including one or more controls for operating the endoscope and including an actuator integrated therein for moving the bite assembly of the biopsy forceps;
        a biopsy lumen configured to receive the biopsy sample obtained with the biopsy forceps; and
        a sample vial cassette removably secured to the handle, the sample vial cassette having a plurality of sample chambers into which a sample vial is removably disposed, wherein the sample vial cassette is movable with respect to an opening in the handle so as to move a sample vial within the sample vial cassette to a position within the handle so as to be aligned with a proximal end of the biopsy lumen;
        wherein the biopsy lumen is coupleable to means for retrieving the biopsy sample through the biopsy lumen and into the sample vial of the sample vial cassette aligned with the proximal end of the biopsy lumen.

2. The system of claim 1, wherein multiple biopsy samples are individually received in a corresponding number of sample vials without removing the biopsy forceps from the elongated shaft.

3. The system of claim 1, wherein the means for retrieving the biopsy sample is a vacuum source applied to the proximal end of the biopsy lumen.

4. The system of claim 1, wherein the means for retrieving the biopsy sample is a liquid applied at a distal end of the biopsy lumen to flush the biopsy sample through the biopsy lumen.

5. The system of claim 1, wherein the means for retrieving the biopsy sample is a gas applied at a distal end of the biopsy lumen to blow the biopsy sample through the biopsy lumen.

6. The system of claim 1, wherein the shaft of the biopsy forceps includes a hollow lumen that forms the biopsy lumen.

7. The system of claim 1, wherein the bite assembly is actuated with a programmable firing mechanism.

8. The system of claim 1, wherein the bite assembly includes echogenic markings.

9. The system of claim 1, wherein the elongated shaft includes a tool lumen separate from the biopsy lumen, in which the biopsy forceps is placed.

10. The system of claim 1, wherein each sample chamber of the plurality of sample chambers includes a port for forming a connection with the biopsy lumen and a vacuum port configured to permit a vacuum to be selectively applied to the sample chamber.

11. The system of claim 1, wherein the system further comprises a position tracking system for recording a set of reference coordinates that indicate the position where the biopsy sample was obtained.

12. A kit for obtaining multiple biopsy samples, the kit comprising:
    i) a single-use endoscope comprising:
        an elongated shaft;
        a handle permanently fixed and stationary relative to the elongated shaft, the handle including one or more controls for operating the endoscope and including an actuator integrated therein for controlling a biopsy forceps to obtain a biopsy sample, the biopsy forceps being disposed within the elongated shaft;
        a biopsy lumen configured to receive the biopsy sample obtained with the biopsy forceps; and
        a sample chamber integrated within the handle that is in fluid communication with the biopsy lumen in order to receive the biopsy sample from the biopsy lumen; and
    ii) at least one sample vial capable of being removably disposed in the sample chamber for capturing one or more biopsy samples received from the biopsy lumen, the at least one sample vial having a series of removable dividers for separating the one or more biopsy samples.

13. An endoscope comprising:
    an elongated shaft
    a handle permanently fixed and stationary relative to the elongated shaft, the handle including an opening to receive a sample vial and one or more controls for operating the endoscope and for actuating a biopsy forceps to obtain biopsy samples;
    a biopsy lumen having a proximal end that terminates at the opening in the handle and is configured to receive a biopsy samples obtained with the biopsy forceps; and
    a cassette comprising a plurality of removable sample vials, wherein the cassette is secured to the handle and movable thereon to position a sample vial in the opening to receive a biopsy sample from the biopsy lumen.

14. The endoscope of claim 13, wherein the biopsy sample is received through the biopsy lumen by a vacuum source applied to the proximal end of the biopsy lumen.

15. The endoscope of claim 13, wherein the biopsy sample is received through the biopsy lumen by a liquid applied at a distal end of the biopsy lumen to flush the biopsy sample through the biopsy lumen.

16. The endoscope of claim 13, wherein the biopsy sample is received through the biopsy lumen by a gas applied at a distal end of the biopsy lumen to blow the biopsy sample through the biopsy lumen.

17. The endoscope of claim 13, wherein the biopsy forceps includes a shaft having a hollow lumen that forms the biopsy lumen.

18. The endoscope of claim 13, wherein the biopsy forceps are actuated with a programmable firing mechanism.

19. The endoscope of claim 13, wherein the elongated shaft includes a tool lumen separate from the biopsy lumen, in which the biopsy forceps is placed.

20. The endoscope of claim 13, wherein the cassette includes a port for forming a connection with the biopsy lumen and a vacuum port configured to permit a vacuum to be selectively applied to the biopsy lumen to retrieve the biopsy sample.

21. A single use endoscope system comprising:
an endoscope configured for multiple biopsy sample collection, the endoscope comprising:
   an elongated shaft;
   a handle permanently fixed and stationary relative to the elongated shaft, the handle including one or more controls for operating the endoscope and an actuator integrated therein for moving a bite assembly on a biopsy forceps to obtain a biopsy sample,
   the biopsy forceps including a shaft having a biopsy lumen configured to receive the biopsy sample obtained with the biopsy forceps;
   a sample vial cassette removably coupled to the handle, the sample vial cassette having a plurality of sample vials that are selectively positioned by movement of the cassette into an opening within the handle to be in fluid communication with the biopsy lumen in order to receive the biopsy sample from the biopsy lumen; and
   means for retrieving the biopsy sample through the biopsy lumen and into a sample vial that is removably inserted into a sample chamber of the sample vial cassette.

22. A multiple biopsy endoscope comprising:
an elongated shaft
a biopsy forceps disposed within the elongated shaft having a bite assembly that is movable to obtain a biopsy sample;
a biopsy lumen in the shaft of the endoscope that receives the biopsy sample obtained with the biopsy forceps;
a handle permanently fixed and stationary relative to the elongated shaft, the handle including one or more controls for operating the endoscope and including an actuator integrated therein for moving the bite assembly of the biopsy forceps; and
a sample cassette including an array of sample vials removably received therein, wherein the sample cassette is secured to and moveable on the handle to selectively position each removable sample vial of the array in an opening in the handle in fluid communication with the biopsy lumen to receive the biopsy sample.

23. The kit of claim 12, wherein the series of removable dividers are positioned axially along a length of the at least one sample vial.

24. The kit of claim 12, further including an imaging system at or adjacent a distal end of the elongated shaft.

25. The endoscope of claim 13, further including an imaging system at or adjacent a distal end of the elongated shaft.

26. The system of claim 21, further including an imaging system at or adjacent a distal end of the elongated shaft.

27. The endoscope of claim 22, further including an imaging system at or adjacent a distal end of the elongated shaft.

* * * * *